United States Patent
Crouse et al.

(10) Patent No.: US 8,383,786 B2
(45) Date of Patent: Feb. 26, 2013

(54) PESTICIDAL COMPOSITIONS

(75) Inventors: Gary D. Crouse, Noblesville, IN (US);
Thomas C. Sparks, Greenfield, IN (US);
CaSandra Lee McLeod, Indianapolis, IN (US); David A. Demeter, Fishers, IN (US); Zoltan L. Benko, Indianapolis, IN (US); Debra L. Camper, Indianapolis, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 438 days.

(21) Appl. No.: 12/703,880

(22) Filed: Feb. 11, 2010

(65) Prior Publication Data

US 2010/0204164 A1    Aug. 12, 2010

Related U.S. Application Data

(60) Provisional application No. 61/151,543, filed on Feb. 11, 2009.

(51) Int. Cl.
| | |
|---|---|
| C07H 15/203 | (2006.01) |
| C07H 15/00 | (2006.01) |
| C07H 17/02 | (2006.01) |
| A61K 31/7034 | (2006.01) |
| A61K 31/7042 | (2006.01) |
| A61K 31/70 | (2006.01) |
| A61K 31/415 | (2006.01) |
| C07D 309/00 | (2006.01) |

(52) U.S. Cl. ......... 536/17.4; 536/4.1; 536/18.1; 514/25; 514/183; 514/247; 549/417

(58) Field of Classification Search .............. 536/17.4, 536/4.1, 18.1; 514/25, 183, 247; 549/417
See application file for complete search history.

(56) References Cited

U.S. PATENT DOCUMENTS

2009/0209476 A1    8/2009   Crouse et al.

FOREIGN PATENT DOCUMENTS

| WO | WO 98/47894 A1 | 10/1998 |
| WO | PCT/US2009/033711 | 7/2009 |
| WO | WO2010/093752 | 8/2010 |

OTHER PUBLICATIONS

L. Zhou et al.: "Metabolites of an Orally Active Antimicrobial Prodrug, 2,5-Bis(4-Amidophenyl) Furan-Bis-0-Methylam Idoxime, Identified by Liquid Chromatography/Tandem Mass Spectrometry" J. Mass Spectrom., vol. 39, 2004, pp. 351-360, XP002536691 the whole document.

Yuan J J et al: "Disposition of a specific cyclooxygenase-2 inhibitor valdecoxib, in human" Drug Metabolism and Disposition, Williams and Wilkins, Baldimore, MD, US, vol. 30, No. 9, Jan. 1, 2002, pp. 1013-1021, XP002311613.

*Primary Examiner* — Shaojia Anna Jiang
*Assistant Examiner* — Michael C Henry
(74) *Attorney, Agent, or Firm* — Carl D. Corvin

(57) ABSTRACT

The invention disclosed in this document is related to the field of pesticides and their use in controlling pests. A compound having the following structure is disclosed.

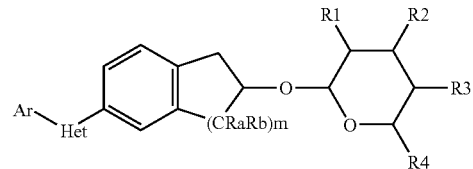

4 Claims, No Drawings

PESTICIDAL COMPOSITIONS

This application claims the benefit of U.S. Provisional Application Ser. No. 61/151,543 filed on 11 Feb. 2009, the entire disclosure of which is hereby incorporated by reference. The invention disclosed in this document is related to the field of pesticides and their use in controlling pests.

FIELD OF THE INVENTION

Background of the Invention

Pests cause millions of human deaths around the world each year. Furthermore, there are more than ten thousand species of pests that cause losses in agriculture. These agricultural losses amount to billions of U.S. dollars each year. Termites cause damage to various structures such as homes. These termite damage losses amount to billions of U.S. dollars each year. As a final note, many stored food pests eat and adulterate stored food. These stored food losses amount to billions of U.S. dollars each year, but more importantly, deprive people of needed food.

There is an acute need for new pesticides. Insects are developing resistance to pesticides in current use. Hundreds of insect species are resistant to one or more pesticides. The development of resistance to some of the older pesticides, such as DDT, the carbamates, and the organophosphates, is well known. But resistance has even developed to some of the newer pesticides. Therefore, a need exists for new pesticides and particularly for pesticides that have new modes of action.

SUBSTITUENTS

Non-Exhaustive List

The examples given for the substituents are (except for halo) non-exhaustive and must not be construed as limiting the invention disclosed in this document.

"Alkenyl" means an acyclic, unsaturated (at least one carbon-carbon double bond), branched or unbranched, substituent consisting of carbon and hydrogen, for example, vinyl, allyl, butenyl, pentenyl, hexenyl, heptenyl, octenyl, nonenyl, and decenyl.

"Alkenyloxy" means an alkenyl further consisting of a carbon-oxygen single bond, for example, allyloxy, butenyloxy, pentenyloxy, hexenyloxy, heptenyloxy, octenyloxy, nonenyloxy, and decenyloxy.

"Alkoxy" means an alkyl further consisting of a carbon-oxygen single bond, for example, methoxy, ethoxy, propoxy, isopropoxy, 1-butoxy, 2-butoxy, isobutoxy, tert-butoxy, pentoxy, 2-methylbutoxy, 1,1-dimethylpropoxy, hexoxy, heptoxy, octoxy, nonoxy, and decoxy.

"Alkyl" means an acyclic, saturated, branched or unbranched, substituent consisting of carbon and hydrogen, for example, methyl, ethyl, propyl, isopropyl, 1-butyl, 2-butyl, isobutyl, tert-butyl, pentyl, 2-methylbutyl, 1,1-dimethylpropyl, hexyl, heptyl, octyl, nonyl, and decyl.

"Alkynyl" means an acyclic, unsaturated (at least one carbon-carbon triple bond, and any double bonds), branched or unbranched, substituent consisting of carbon and hydrogen, for example, ethynyl, propargyl, butynyl, pentynyl, hexynyl, heptynyl, octynyl, nonynyl, and decynyl.

"Halo" means fluoro, chloro, bromo, and iodo.

"Haloalkoxy" means a haloalkyl further consisting of a carbon-oxygen single bond, for example, fluoromethoxy, difluoromethoxy, and trifluoromethoxy, 2-fluoroethoxy, 1,1,2,2,2-pentafluoroethoxy, 1,1,2,2-tetrafluoro-2-bromoethoxy and 1,1,2,2-tetrafluoroethoxy.

"Haloalkyl" means an alkyl further consisting of, from one to the maximum possible number of, identical or different, halos, for example, fluoromethyl, difluoromethyl, trifluoromethyl, 2-fluoroethyl, 2,2,2-trifluoroethyl, chloromethyl, trichloromethyl, and 1,1,2,2-tetrafluoroethyl.

"Halophenyloxy" means a phenyloxy having one or more, identical or different, halos.

"Hydroxyalkyl" means an alkyl having one or more hydroxy groups.

DETAILED DESCRIPTION OF THE INVENTION

The compounds of this invention have the following formula:

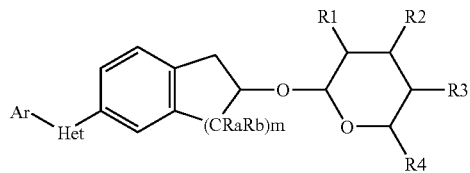

where

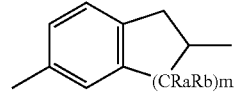

is referred to as Ar2
wherein:
 (a) Ar is
 (1) furanyl, phenyl, pyridazinyl, pyridyl, pyrimidinyl, thiadiazolyl, thienyl, or
 (2) substituted furanyl, substituted phenyl, substituted pyridazinyl, substituted pyridyl, substituted pyrimidinyl, substituted thiadiazolyl, or substituted thienyl,
  wherein said substituted furanyl, substituted phenyl, substituted pyridazinyl, substituted pyridyl, substituted pyrimidinyl, substituted thiadiazolyl, and substituted thienyl, have one or more substituents independently selected from H, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, S(=O)($C_1$-$C_6$ alkyl), S(=O)$_n$($C_1$-$C_6$ haloalkyl), $OSO_2$($C_1$-$C_6$ alkyl), $OSO_2$($C_1$-$C_6$ haloalkyl), C(=O) H, C(=O)$NR_xR_y$, ($C_1$-$C_6$ alkyl)$NR_xR_y$, C(=O)($C_1$-$C_6$ alkyl), C(=O)O($C_1$-$C_6$ alkyl), C(=O)($C_1$-$C_6$ haloalkyl), C(=O)O($C_1$ haloalkyl), C(=O)($C_3$-$C_6$ cycloalkyl), C(=O)O($C_3$-$C_6$ cycloalkyl), C(=O) ($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), phenyl, phenoxy, substituted phenyl and substituted phenoxy (wherein such substituted phenyl and substituted phenoxy have one or more substituents independently selected from H, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n$ ($C_1$-$C_6$ alkyl), $S(=O)_n$($C_1$-$C_6$ haloalkyl), $OSO_2$($C_1$-$C_6$ alkyl), $OSO_2$($C_1$-$C_6$ haloalkyl), C(=O)H, C(=O)$NR_xR_y$, ($C_1$-$C_6$ alkyl)$NR_xR_y$, C(=O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl)phenyl, and phenoxy);

(b) Het is a 5 or 6 membered, saturated or unsaturated, heterocyclic ring, containing one or more heteroatoms independently selected from nitrogen, sulfur, or oxygen, and where Ar and Ar2 are not ortho to each other (but may be meta or para, such as, for a five membered ring they are 1,3 and for a 6 membered ring they are either 1, 3 or 1,4), and where said heterocyclic ring may also be substituted with one or more substituents independently selected from H, F, Cl, Br, I, CN, $NO_2$, oxo, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n$($C_1$-$C_6$ alkyl), $S(=O)_n$($C_1$-$C_6$ haloalkyl), $OSO_2$($C_1$-$C_6$ alkyl), $OSO_2$($C_1$-$C_6$ haloalkyl), C(=O)H, C(=O)$NR_xR_y$, ($C_1$-$C_6$ alkyl)$NR_xR_y$, C(=O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), phenyl, phenoxy, substituted phenyl and substituted phenoxy (wherein such substituted phenyl and substituted phenoxy have one or more substituents independently selected from H, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)$($C_1$-$C_6$ alkyl), $S(=O)_n$($C_1$-$C_6$ haloalkyl), $OSO_2$($C_1$-$C_6$ alkyl), $OSO_2$($C_1$-$C_6$ haloalkyl), C(=O)H, C(=O)$NR_xR_y$, ($C_1$-$C_6$ alkyl)$NR_xR_y$, C(=O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), phenyl, and phenoxy);

(c) R1 is H, OH, F, Cl, Br, I, oxo, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_2$-$C_6$ alkenyloxy, ($C_1$-$C_6$ alkyl)O($C_1$-$C_6$ alkyl), ($C_1$-$C_6$ alkyl)O($C_1$-$C_6$ alkoxy), OC(=O)($C_1$-$C_6$ alkyl), OC(=O)($C_3$-$C_6$ cycloalkyl), OC(=O)($C_1$-$C_6$ haloalkyl), OC(=O)($C_2$-$C_6$ alkenyl), or $NR_xR_y$;

(d) $R_2$ is H, F, Cl, Br, I, oxo, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_2$-$C_6$ alkenyloxy, ($C_1$-$C_6$ alkyl)O($C_1$-$C_6$ alkyl), ($C_1$-$C_6$ alkyl)O($C_1$-$C_6$ alkoxy), OC(=O)($C_1$-$C_6$ alkyl), OC(=O)($C_3$-$C_6$ cycloalkyl), OC(=O)($C_1$-$C_6$ haloalkyl), OC(=O)($C_2$-$C_6$ alkenyl), or $NR_xR_y$;

(e) $R_3$ is H, OH, F, Cl, Br, I, oxo, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_2$-$C_6$ alkenyloxy, ($C_1$-$C_6$ alkyl)O($C_1$-$C_6$ alkyl), ($C_1$-$C_6$ alkyl)O($C_1$-$C_6$ alkoxy), OC(=O)($C_1$-$C_6$ alkyl), OC(=O)($C_3$-$C_6$ cycloalkyl), OC(=O)($C_1$-$C_6$ haloalkyl), OC(=O)($C_2$-$C_6$ alkenyl), or $NR_xR_y$;

(f) R4 is H, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyloxy, ($C_1$-$C_6$ alkyl)O($C_1$-$C_6$ alkyl);

(g) m is 1 or 2;

(h) $R_x$ and $R_y$ are independently selected from H, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n$($C_1$-$C_6$ alkyl), $S(=O)_n$($C_1$-$C_6$ haloalkyl), $OSO_2$($C_1$-$C_6$ alkyl), $OSO_2$($C_1$-$C_6$ haloalkyl), C(=O)H, C(=O)OH, C(=O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), phenyl, and phenoxy; and (i) $R_a$ and $R_b$ are independently selected from H, $C_1$-$C_6$ alkyl, $C_1$-$C_6$ haloalkyl, $C_1$-$C_6$ hydroxyalkyl, $C_1$-$C_6$ alkoxy, and $C_1$-$C_6$ haloalkoxy.

In another embodiment of this invention:

(a) Ar is phenyl, pyridazinyl, pyridyl, thienyl, substituted phenyl, substituted pyridazinyl, substituted pyridyl, substituted thiadiazolyl, or substituted thienyl, wherein said substituted phenyl, substituted pyridazinyl, substituted pyridyl, and substituted thienyl, have one or more substituents independently selected from F, Cl, Br, I, CN, $NO_2$, $C_1$-$C_6$ alkyl, $C_1$-$C_6$ haloalkyl, $C_1$-$C_6$ hydroxyalkyl, $C_1$-$C_6$ haloalkoxy, $C_2$-$C_6$ alkenyl, $S(=O)$($C_1$-$C_6$ alkyl), $S(=O)_n$($C_1$-$C_6$ haloalkyl), $OSO_2$ ($C_1$-$C_6$ haloalkyl), C(=O)($C_1$-$C_6$ alkyl), ($C_1$-$C_6$ alkyl)S($C_1$-$C_6$ alkyl), and phenoxy (wherein such substituted phenoxy has one or more substituents independently selected from F, Cl, Br, or I).

In another embodiment of the invention:

(a) Ar is substituted phenyl, substituted pyridyl, or substituted thiadiazolyl, wherein said substituted phenyl, substituted pyridyl, and substituted thiadiazolyl, have one or more substituents independently selected from F, Cl, Br, I, CN, $NO_2$, $C_1$-$C_6$ alkyl, $C_1$-$C_6$ haloalkyl, $C_1$-$C_6$ hydroxyalkyl, $C_1$-$C_6$ haloalkoxy, $C_2$-$C_6$ alkenyl, $S(=O)_n$($C_1$-$C_6$ alkyl), $S(=O)_n$($C_1$-$C_6$ haloalkyl), $OSO_2$($C_1$-$C_6$ haloalkyl), C(=O) ($C_1$-$C_6$ alkyl), ($C_1$-$C_6$ alkyl)S($C_1$-$C_6$ alkyl), and phenoxy (wherein such substituted phenoxy has one or more substituents independently selected from F, Cl, Br, or I).

In another embodiment of the invention:

(a) Ar is substituted phenyl wherein said substituted phenyl has one or more substituents independently selected from F, Cl, Br, I, $C_1$-$C_6$ alkyl, $C_1$-$C_6$ haloalkyl, $C_1$-$C_6$ alkoxy, and $C_1$-$C_6$ haloalkoxy.

In another embodiment of this invention Ar is phenyl or pyridyl.

In another embodiment of the invention:

(b) Het is imidazolyl, isothiazolyl, isoxazolyl, 1,2,4-oxadiazolyl, 1,3,4-oxadiazolyl, oxazolinyl, oxazolyl, piperazinyl, piperidinyl, pyrazinyl, pyrazolinyl, pyrazolyl, pyridazinyl, pyridyl, pyrimidinyl, pyrrolyl, 1,2,3,4-tetrazolyl, thiadiazolyl, thiazolinyl, thiazolyl, 1,2,3-triazinyl, 1,2,4-triazinyl, 1,3,5-triazinyl, 1,2,3-triazolyl, 1,2,4-triazolyl, substituted imidazolyl, substituted isothiazolyl, substituted isoxazolyl, substituted 1,2,4-oxadiazolyl, substituted 1,3,4 oxadiazolyl, substituted oxazolinyl, substituted oxazolyl, substituted piperazinyl, substituted piperidinyl, substituted pyrazinyl, substituted pyrazolinyl, substituted pyrazolyl, substituted pyridazinyl, substituted pyridyl, substituted pyrimidinyl, substituted pyrrolyl, substituted tetrazolyl, substituted thiadiazolyl, substituted thiazolinyl, substituted thiazolyl, substituted 1,2,3-triazinyl, substituted 1,2,4-triazinyl, substituted 1,3,5-triazinyl, substituted 1,2,3-triazolyl, and substituted 1,2,4-triazolyl, where said substituted groups have one or more substituents independently selected from H, F, Cl, Br, I, CN, NO$_2$, oxo, C$_1$-C$_6$ alkyl, C$_1$-C$_6$ haloalkyl, C$_1$-C$_6$ hydroxyalkyl, C$_3$-C$_6$ cycloalkyl, C$_3$-C$_6$ halocycloalkyl, C$_3$-C$_6$ hydroxycycloalkyl, C$_3$-C$_6$ cycloalkoxy, C$_3$-C$_6$ halocycloalkoxy, C$_3$-C$_6$ hydroxycycloalkoxy, C$_1$-C$_6$ alkoxy, C$_1$-C$_6$ haloalkoxy, C$_2$-C$_6$ alkenyl, C$_2$-C$_6$ alkynyl, S(=O)(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)H, C(=O)NR$_x$R$_y$, (C$_1$-C$_6$ alkyl)NR$_x$R$_y$, C(=O)(C$_1$-C$_6$ alkyl), C(=O)O(C$_1$-C$_6$ alkyl), C(=O)(C$_1$-C$_6$ haloalkyl), C(=O)(C$_3$-C$_6$ cycloalkyl), C(=O)O(C$_3$-C$_6$ cycloalkyl), C(=O)(C$_1$-C$_6$ haloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_2$-C$_6$ alkyl), C(=O)(C$_1$-C$_6$ alkyl)C(=O)O(C$_1$-C$_6$ alkyl)phenyl, phenoxy, substituted phenyl and substituted phenoxy (wherein such substituted phenyl and substituted phenoxy have one or more substituents independently selected from H, F, Cl, Br, I, CN, NO$_2$, oxo, C$_1$-C$_6$ alkyl, C$_1$-C$_6$ haloalkyl, C$_1$-C$_6$ hydroxyalkyl, C$_3$-C$_6$ cycloalkyl, C$_3$-C$_6$ halocycloalkyl, C$_3$-C$_6$ hydroxycycloalkyl, C$_3$-C$_6$ cycloalkoxy, C$_3$-C$_6$ halocycloalkoxy, C$_3$-C$_6$ hydroxycycloalkoxy, C$_1$-C$_6$ alkoxy, C$_1$-C$_6$ haloalkoxy, C$_2$-C$_6$ alkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)H, C(=O)NR$_x$R$_y$, (C$_1$-C$_6$ alkyl)NR$_x$R$_y$, C(=O)(C$_1$-C$_6$ alkyl), C(=O)O(C$_1$-C$_6$ alkyl), C(=O)(C$_1$-C$_6$ haloalkyl), C(=O)(C$_3$-C$_6$ cycloalkyl), C(=O)O(C$_3$-C$_6$ cycloalkyl), C(=O)(C$_1$-C$_6$ haloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl)phenyl, and phenoxy).

In another embodiment of this invention:

(b) Het is imidazolyl, isoxazolyl, 1,2,4-oxadiazolyl, 1,3,4-oxadiazolyl, oxazolyl, piperazinyl, pyrazinyl, pyrazolyl, pyridazinyl, pyridyl, pyrimidinyl, pyrrolyl, 1,2,3,4-tetrazolyl, thiadiazolyl, thiazolyl, 1,2,4-triazinyl, 1,3,5-triazinyl, 1,2,3-triazolyl, 1,2,4-triazolyl, substituted imidazolyl, substituted 1,3,4-oxadiazolyl, substituted piperazinyl, substituted pyrazolyl, substituted pyrimidinyl, and substituted 1,2,4-triazolyl, where said substituted groups have one or more substituents independently selected from F, Cl, Br, I, CN, NO$_2$, oxo, C$_1$-C$_6$ alkyl, C$_1$-C$_6$ haloalkyl, C$_1$-C$_6$ hydroxyalkyl, C$_1$-C$_6$ alkoxy, C$_1$-C$_6$ haloalkoxy, C$_2$-C$_6$ alkenyl, S(=O)$_n$(C$_1$-C$_6$ alkyl), S(=O)$_n$(C$_1$-C$_6$ haloalkyl), OSO$_2$(C$_1$-C$_6$ haloalkyl), C(=O)O(C$_1$-C$_6$ alkyl), and (C$_1$-C$_6$ alkyl)S(C$_1$-C$_6$ alkyl), In another embodiment of this invention: (b) Het is pyrimidinyl and pyrazolyl.

In another embodiment of this invention: (c) R1 is a C$_1$-C$_6$ alkoxy.

In another embodiment of this invention: (d) R2 is a C$_1$-C$_6$ alkoxy.

In another embodiment of this invention: (e) R3 is a C$_1$-C$_6$ alkoxy.

In another embodiment of this invention: (f) R4 is a C$_1$-C$_6$ alkyl.

While these embodiments have been expressed, other embodiments and combinations of these expressed embodiments and other embodiments, are possible.

Preparation of Pyranose-Intermediates

A wide variety of pyranoses (in different structural forms, for example, D- and L-) can be used to make the compounds of this invention. For example, the following non-exhaustive list of pyranoses may be used: ribose, arabinose, xylose, lyxose, ribulose, xylulose, allose, altrose, glucose, mannose, gulose, idose, galactose, talose, psicose, fructose, sorbose, tagatose, fucose, mycarose, quinovose, oleandrose, rhamnose, and paratose. In most of the examples below, L-rhamnose was used to make pyranose-intermediates.

In general, pyranose-intermediates can be made as follows (using L-rhamnose as an example). O-Alkylated rhamnose derivatives can be prepared from commercially available L-rhamnose or L-rhamnose hydrate by using an alkyl iodide and powdered potassium hydroxide (KOH) in dry dimethyl sulfoxide (DMSO) at from 5° C. to 15° C. The fully alkylated product is then isolated by extraction of the DMSO solution with hexanes, followed by concentration of the hexane layer under vacuum. This intermediate alkyl pyranoside is then treated directly with aqueous hydrochloric acid (HCl) or other aqueous acid, which forms the free hydroxy sugar, usually as a mixture of a and p anomers.

Alternatively, the per-alkylated L-rhamnose can be isolated by hydrolysis of spinosad or other tri-(O-alkyl)rhamnosylated natural product, using conditions similar to those described for the isolation of methyl oleandroside from avermectin B$_2$ (Loewe et al., *J. Org. Chem.* 1994, 59, 7870). Thus, treatment of technical spinosad with excess concentrated sulfuric acid in dry methyl alcohol (MeOH) results in hydrolysis of the rhamnose sugar and conversion into the methylpyranoside. The pure methylpyranoside can then be removed from the reaction medium by exhaustive extraction with hexanes or other hydrocarbon solvent. The pure rhamnopyranoside can then be isolated in ca. 65-75% overall yield by distillation of the crude liquor under vacuum.

The 3-O-ethyl 2,4-di-O-methyl rhamnose can be prepared in a similar manner, starting from spinetoram. Other alkylated derivatives can be likewise produced by starting with the appropriately functionalized spinosoid derivatives, which are made from any spinosyn factor which has one or more free hydroxyl groups attached to rhamnose (for example, spinosyn J) using conditions described in DeAmicis et al., U.S. Pat. No. 6,001,981, 1999.

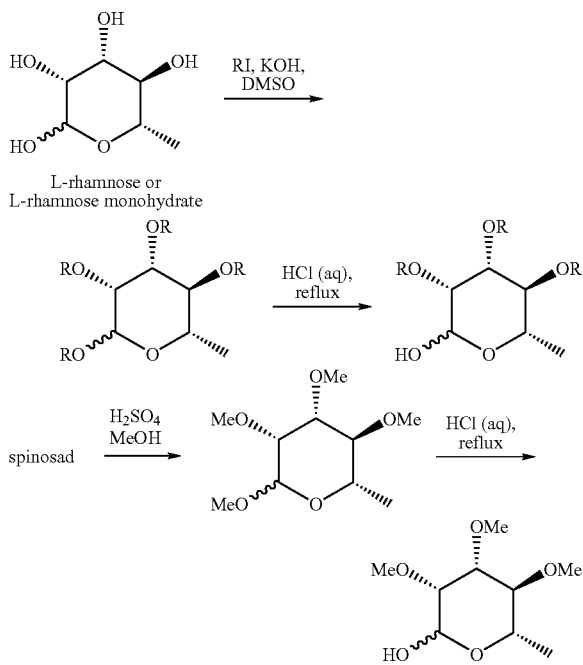

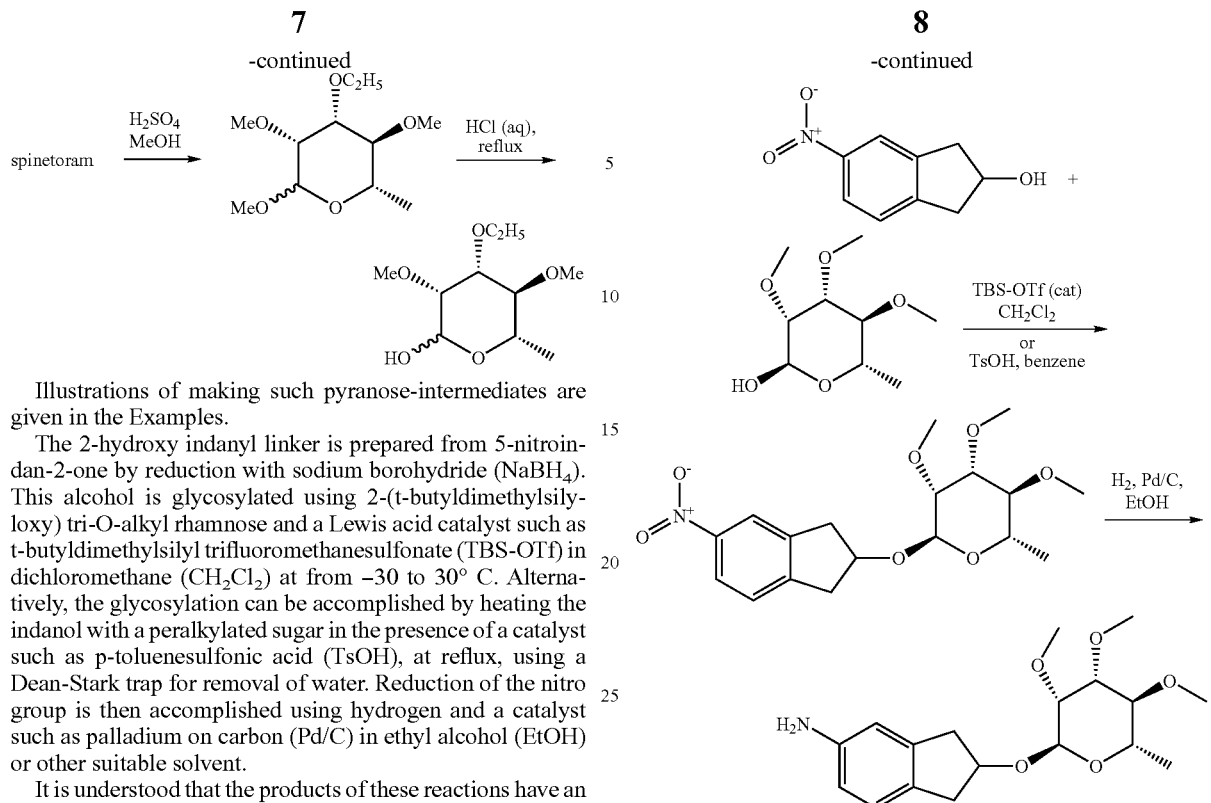

Illustrations of making such pyranose-intermediates are given in the Examples.

The 2-hydroxy indanyl linker is prepared from 5-nitroindan-2-one by reduction with sodium borohydride ($NaBH_4$). This alcohol is glycosylated using 2-(t-butyldimethylsilyloxy) tri-O-alkyl rhamnose and a Lewis acid catalyst such as t-butyldimethylsilyl trifluoromethanesulfonate (TBS-OTf) in dichloromethane ($CH_2Cl_2$) at from −30 to 30° C. Alternatively, the glycosylation can be accomplished by heating the indanol with a peralkylated sugar in the presence of a catalyst such as p-toluenesulfonic acid (TsOH), at reflux, using a Dean-Stark trap for removal of water. Reduction of the nitro group is then accomplished using hydrogen and a catalyst such as palladium on carbon (Pd/C) in ethyl alcohol (EtOH) or other suitable solvent.

It is understood that the products of these reactions have an additional optical center, and that the products therefore consist of a diastereomeric mixture.

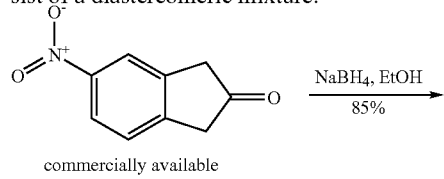

Other indanyl-tri-O-methylrhamnose intermediates and target compounds can be prepared as shown below. 2-Indanol is O-acetylated as described in the literature (Inamato, *Can. J. Chem.* 1967, 45, 1185). Friedel-Crafts acetylation, followed by basic hydrolysis, then gives the acetylated 2-indanol which is condensed with the t-butyldimethylsilyl (TBDMS) ether of the tri-O-methylrhamnose acetal using trimethylsilyl triflate (TMSOTf) catalyst.

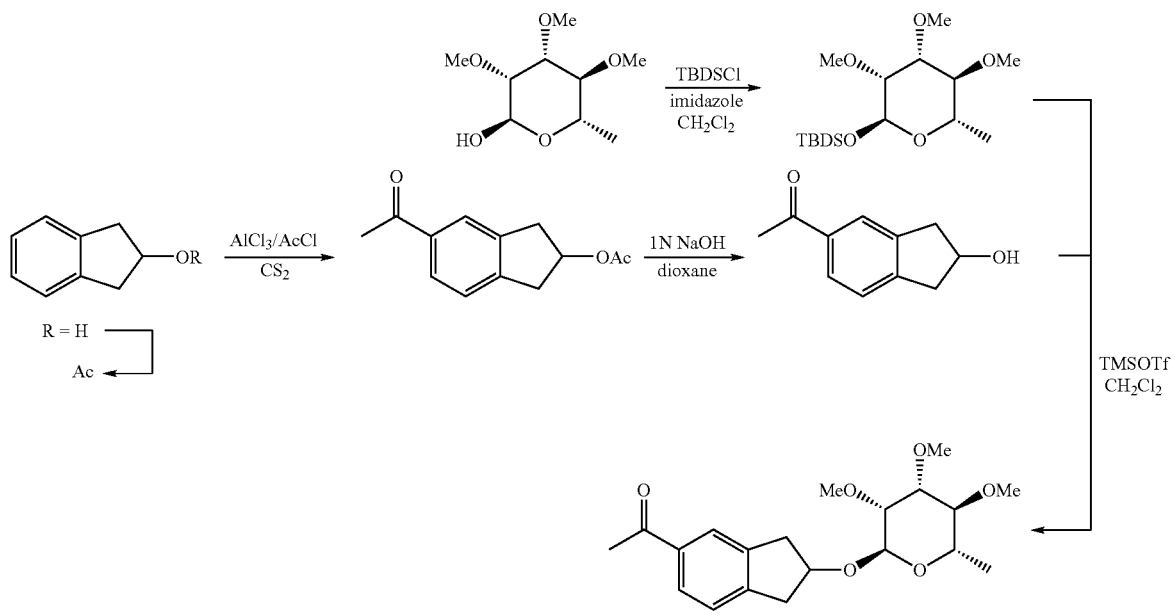

Conversion of the acetyl group into a pyrimidine or a pyrazole is accomplished in two stages. In the first stage, a 2-(dimethylamino) acryloyl group is formed by treatment of the acetyl derivative with dimethylformamide dimethyl acetal (DMF-DMA). The enaminone is then converted either into a pyrimidine, by treatment with an appropriately substituted benzamidine, or into a pyrazole by treatment with hydrazine in an alcohol solvent such as EtOH or MeOH. Further N-arylation of the pyrazole with a haloaromatic group can then be accomplished by using a base such as KOH, potassium carbonate ($K_2CO_3$), cesium carbonate ($Cs_2CO_3$), sodium hydride (NaH), or lithium hexamethyldisilazide (LiHMDS) in a polar aprotic solvent (for example, Liu et al., *J. Org. Chem.* 2005, 70, 10135.)

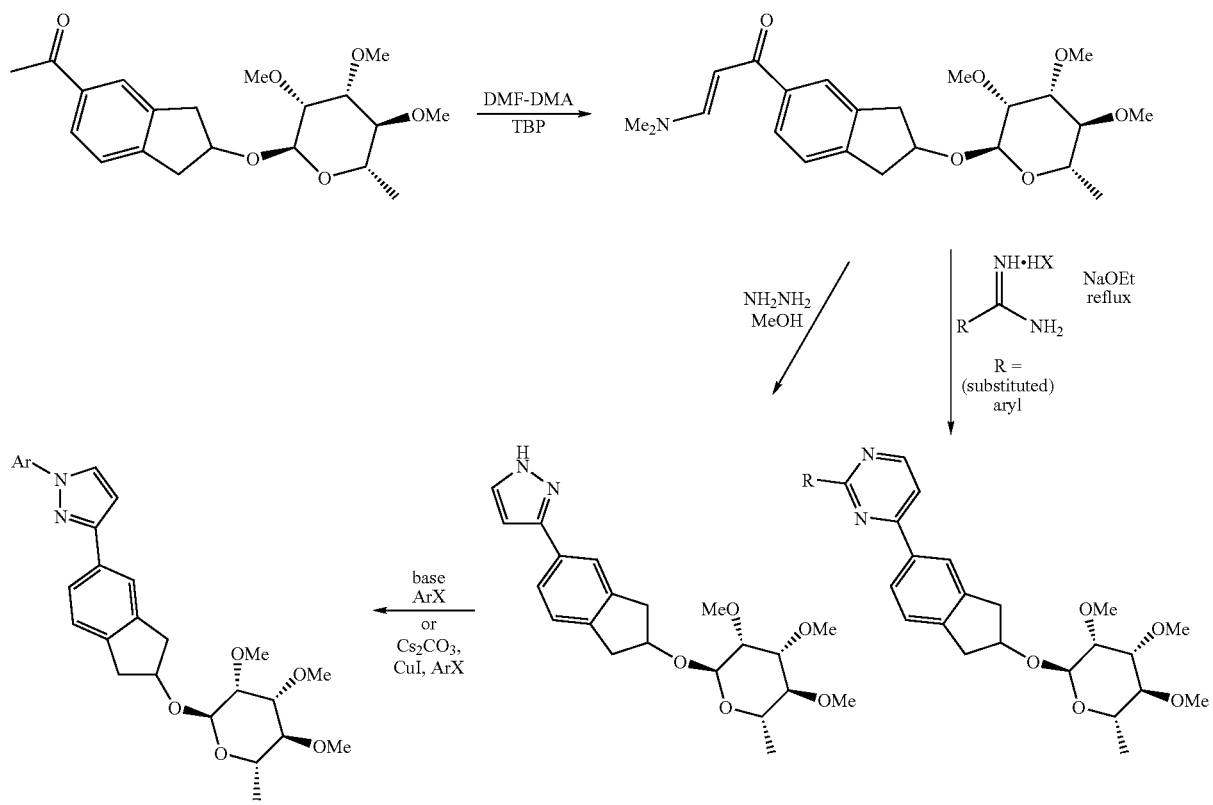

2-Indanols substituted with a variety of alternative heterocycles are also within the scope of this invention. By condensing a halo-substituted indanol with an amino heterocycle, these can be achieved. A wide range of NH-substituted heterocycles (imidazoles, triazoles, pyrazoles, etc.), and a wide range of coupling conditions, have been described in recent literature.

In addition, 2-hydroxy tetrahydronaphthyl derivatives also serve as precursors for compounds of this invention. The commercially available 6-bromo-2-tetralone can be converted into the corresponding 2-O-glycosylated intermediate, which can then be coupled to an appropriate heterocyclic moiety by any of a variety of methods in the literature including, but not limited to, Ullmann coupling (where the heterocycle contains a free —NH— group), or Suzuki coupling (where the heterocycle contains a boronic acid or ester group).

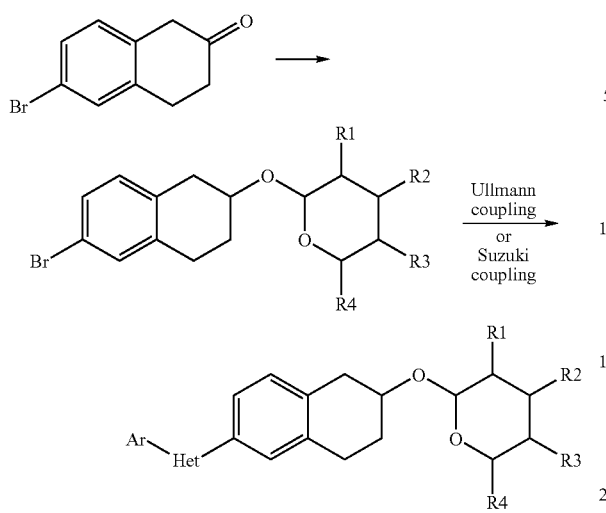

EXAMPLES

These examples are for illustration purposes and are not to be construed as limiting the invention disclosed in this document to only the embodiments disclosed.

Example 1

Preparation of (3R,4R,5S,6S)-2,3,4,5-tetramethoxy-6-methyl-tetrahydropyran (Compound E-1)

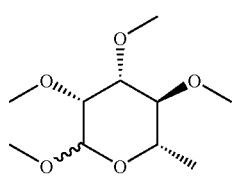

A solution of L-rhamnose hydrate (40 grams (g), 0.22 mole (mol)) in dry dimethyl sulfoxide (DMSO; 450 milliliters (mL)) was placed in a 2-liter (L) 3-neck round bottom flask and stirred mechanically while powdered potassium hydroxide (KOH; 75 g, 1.34 mol) was added in one portion. Iodomethane (187 g, 1.32 mol) was added to this solution at a rate such that the temperature of the solution was maintained below 30° C. A dry ice-acetone bath was used intermittently to maintain this temperature. After the addition was complete (about 2 hours (h)), the solution was stirred an additional 3 h, then it was allowed to stand at ambient temperature overnight. This clear solution was then extracted with hexanes (4×500 mL), and the combined hexane solution was washed with brine before drying and evaporation of solvent to provide a light orange solution (44 g, 92%). Distillation gave 40 g of a colorless oil, by 150° C. (0.5 mm Hg).

Example 2

Preparation of (3R,4R,5S,6S)-3,4,5-trimethoxy-6-methyl-tetrahydropyran-2-ol (Compound E-2)

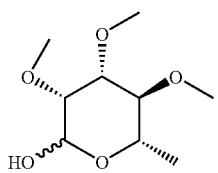

A solution of E-1 (35.7 g, 0.162 mol) in 2 N hydrochloric acid (HCl; 300 mL) was heated at 98° C. for 5 h, was then cooled to room temperature, and was extracted with dichloromethane ($CH_2Cl_2$; 4×170 mL). The combined extracts were dried over magnesium sulfate ($MgSO_4$) and decolorized with charcoal. Concentration gave the title compound (24.7 g, 74%) as a viscous oil. A portion of the crude product (960 milligrams (mg)) was vacuum distilled using a Kuhgelrohr apparatus collecting 890 mg at 145-155° C. (1-2 mm).

Example 3

Preparation of (3R,4R,5S,6S)-4-ethoxy-2,3,5-trimethoxy-6-methyl-tetrahydropyran (Compound E-3)

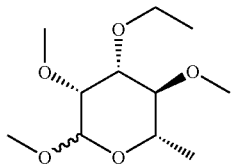

Sulfuric acid ($H_2SO_4$, 98%; 300 mL, 5.6 mol) was added slowly to a stirred solution of methyl alcohol (2.5 L) in a 4-L Erlenmeyer flask. When the solution had cooled to ambient temperature, 3'-OEt spinosyn J/L (350 g, 0.47 mol prepared as in DeAmicis et al., U.S. Pat. No. 6,001,981, 1999) was added and the resulting solution was heated at reflux for 6 h. The cooled solution was transferred to a 4-L separatory funnel and extracted with hexanes (3×1 L). The combined organic solution was dried, concentrated in vacuo, and then distilled using a Kugelrohr apparatus to provide a colorless oil (65 g, 60%), by 165° C. (10 mTorr).

Compounds E-3 through E-22 were made in accordance with the procedures described above and illustrated in Examples 1-3. These compounds are listed in Table 1.

Example 4

Preparation of tert-butyl-dimethyl-((2S,3R,4R,5S,6S)-3,4,5-trimethoxy-6-methyl-tetrahydropyran-2-yloxy)-silane. (Compound E-23)

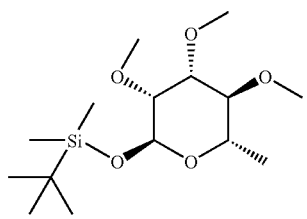 [SMILES: CO[C@@H]1[C@@H](OC)[C@H](C)O[C@@H](O[Si](C)(C)C(C)(C)C)[C@@H]1OC]

Tri-O-methylrhamnose (20.0 g, 97.0 mmol) was dissolved in $CH_2Cl_2$ (400 mL) and treated with imidazole (10.0 g, 147 mmol) and chloro-tert-butyldimethyl silane (TBSCl; 20.0 g, 132 mmol). After 3 days (d), the reaction mixture was partitioned between water ($H_2O$) and $CH_2Cl_2$, and the organic layer was washed with brine, dried over sodium sulfate ($Na_2SO_4$) and concentrated. The crude residue was further purified by chromatography on silica gel (10-20% ethyl acetate (EtOAc) in petroleum ether as eluant) to give the title compound (12.8 g, 82%) as a clear syrup in a 20:80 α:β ratio. The physical properties of the major β-epimer are: $^1$H NMR ($CDCl_3$) δ 4.55 (s, 1H), 3.58 (s, 3H), 3.48 (m, 1H), 3.45 (s, 3H), 3.40 (s, 3H), 3.00 (m, 3H), 1.24 (d, J=6.2 Hz, 3H), 0.80 (s, 9H), 0.05 (s, 6H); EIMS m/z 263 ([M-tBu]$^+$, 1), 88 (100).

Example 5

Preparation of acetic acid 5-acetyl-indan-2-yl ester (Compound E-24)

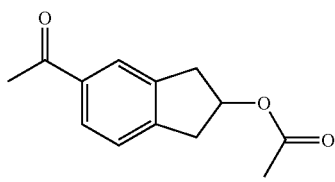 [SMILES: CC(=O)OC1Cc2ccc(C(C)=O)cc2C1]

To a mixture at 5-10° C. of aluminum chloride ($AlCl_3$; 30.6 g, 0.229 mol) in carbon disulfide ($CS_2$; 160 mL) was added acetyl chloride (12 mL, 13.2 g, 0.169 mol). To this mixture was added a solution of acetic acid indan-2-yl ester (19.9 g, 0.113 mol, prepared according to the method described in Can. J. Chem. 1967, 45, 1185) in acetyl chloride (12 mL) keeping the temperature below 11° C. The contents were stirred at 5° C. for 3 h and were then carefully added to ice-water (350 mL) containing concentrated HCl (60 mL). The mixture was extracted with $CH_2Cl_2$ (2×), and the combined extracts were washed with $H_2O$ and were dried over $Na_2SO_4$. Concentration gave the title compound (23.8 g, 97%) as a solid: $^1$H NMR δ 7.84 (s, 1H), 7.82 (m, 1H), 7.32 (d, J=7.0 Hz, 1H), 5.55 (m, 1H), 3.40-3.32 (m, 2H), 3.10-3.05 (m, 2H), 2.60 (s, 3H), 2.04 (s, 3H); EIMS m/z 158 ([M-AcOH]$^+$, 42), 143 (100).

Example 6

Preparation of 1-(2-hydroxy-indan-5-yl)-ethanone (Compound E-25)

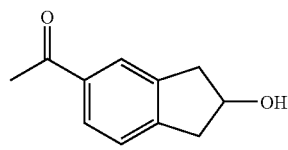

A solution of acetic acid 5-acetyl-indan-2-yl ester (Compound E-24; 1.50 g, 6.87 mmol) in dioxane (7 mL) was treated with 1.0 N sodium hydroxide (NaOH; 7.7 mL), and the solution was stirred at room temperature overnight. The solution was diluted with $H_2O$ (25 mL) and was extracted with $CH_2Cl_2$ (2×). The combined extracts were dried ($MgSO_4$) and concentrated to give the title compound (1.06 g, 88%): $^1$H NMR δ 7.85 (s, 1H), 7.79 (m, 1H), 7.33 (d, J=7.7 Hz, 1H), 4.76 (m, 1H), 3.29-3.21 (m, 2H), 3.00-2.94 (m, 2H), 2.59 (s, 3H), 1.73 (d, J=5.3 Hz, 1H); ELMS m/z 176 (M$^+$, 76), 161 (100).

Example 7

Preparation of 1-[2-((2R,3R,4R,5S,6S)-3,4,5-trimethoxy-6-methyl-tetrahydropyran-2-yloxy)-indan-5-yl]-ethanone (Compound E-26)

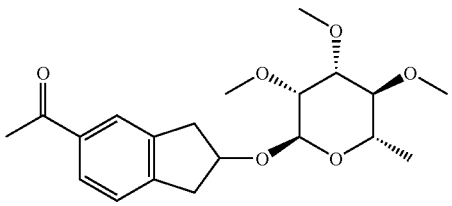 [SMILES: CO[C@@H]1[C@@H](OC)[C@H](C)O[C@@H](OC2Cc3ccc(C(C)=O)cc3C2)[C@@H]1OC]

To a solution at 0-5° C. of 1-(2-hydroxy-indan-5-yl)-ethanone (Compound E-25; 440 mg, 2.50 mmol) and 92% w/w of tert-butyl-dimethyl-(3,4,5-trimethoxy-6-methyl-tetrahydropyran-2-yloxy)-silane (Compound E-23; 1.00 g, 2.87 mmol) in $CH_2Cl_2$ (6 mL) was added via syringe trimethylsilyl triflate (0.12 mL, 146 mg, 0.66 mmol). The contents were allowed to gradually warm to room temperature and were stirred overnight. The solution was diluted with $CH_2Cl_2$ and was washed once with saturated sodium bicarbonate ($NaHCO_3$). The aqueous phase was extracted once with $CH_2Cl_2$, and the combined organics were dried ($MgSO_4$). Concentration gave a pale green oil (783 mg, 86%): $^1$H NMR ($CDCl_3$) δ 7.79 (m, 2H), 7.29 (d, J=7.6 Hz, 1H), 4.97 (s, 1H), 4.64 (m, 1H), 3.67-3.40 (m, 3H), 3.55 (s, 3H), 3.50 (s, 3H), 3.45 (s, 3H), 3.21-2.97 (m, 5H), 2.59 (s, 3H), 1.30 (d, J=6.3 Hz, H); IR (neat) 1683 cm$^{-1}$.

Example 8

Preparation of 3-dimethylamino-1-[2-((2R,3R,4R,5S,6S)-3,4,5-trimethoxy-6-methyl-tetrahydropyran-2-yloxy)-indan-5-yl]-propenone (Compound E-27)

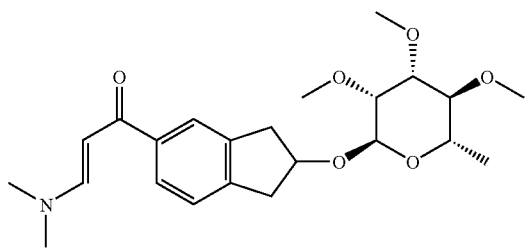

A solution of 1-[2-(3,4,5-trimethoxy-6-methyl-tetrahydropyran-2-yloxy)-indan-5-yl]-ethanone (Compound E-26; 2.02 g, 5.54 mmol) and a trace of 2,4,6-tri-t-butylphenol in dimethylformamide dimethylacetal (DMF-DMA; 12 mL) was heated at 90-100° C. for 48 h. Upon cooling the solution was concentrated to give an oil (2.4 g) which was purified by silica gel chromatography with EtOAc as eluent to remove 620 mg of unreacted starting material. The desired material was then eluted with EtOAc containing 3% triethylamine (Et$_3$N) to afford the title compound (1.5 g, 64%): mp 118-123.5° C.; $^1$H NMR (CDCl$_3$) δ 7.80 (d, J=12.6 Hz, 1H), 7.72 (m, 2H), 7.24 (d, J=7.6 Hz, 1H), 5.70 (d, J=12.6 Hz, 1H), 4.98 (s, 1H), 4.64 (m, 1H), 3.62-3.42 (m, 3H), 3.55 (s, 3H), 3.50 (s, 3H), 3.46 (s, 3H), 3.26-2.95 (m, 5H), 1.32 (d, J=6.3 Hz, 3H); IR (neat) 1644 cm$^{-1}$; ESIMS m/z 420 ([M+H]$^+$); Anal. Calcd for C$_{23}$H$_{33}$NO$_6$: C, 65.84; H, 7.93; N, 3.34. Found: C, 65.36; H, 7.80; N, 3.27.

Example 9

General Procedure to Prepare Pyrimidines

Reaction tubes were charged with 0.714 mmol of the benzamidine hydrohalide, 3 mL of EtOH, 0.76 mL (0.71 mmol) of a 0.93 M solution of sodium ethoxide in EtOH and 1.35 mL (0.24 mmol) of a 0.18 M solution of Compound E-27 in tetrahydrofuran (THF). The mixtures were stirred at 75° C. for 42 h, and then were evaporated to dryness in vacuo. The residues were diluted with ethyl ether (Et$_2$O) and saturated sodium chloride (NaCl). Insoluble material was filtered and the organic phases were washed with saturated NaCl and were dried (MgSO$_4$). Concentration gave crude materials which were purified by chromatography.

The following compounds were prepared using conditions outlined in Example 9.

2-(4-Chlorophenyl)-4-[2-((2R,3R,4R,5S,6S)-3,4,5-trimethoxy-6-methyl-tetrahydropyran-2-yloxy)-indan-5-yl]-pyrimidine (Compound 1C)

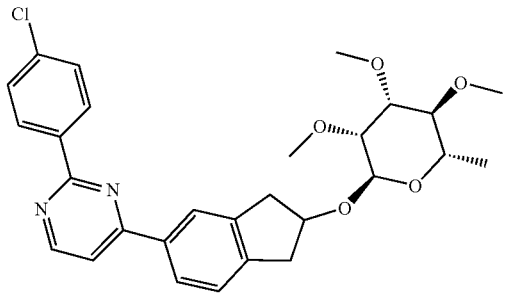 [SMILES: CO[C@@H]1[C@@H](OC)[C@H](C)O[C@@H](OC2Cc3ccc(-c4ccnc(-c5ccc(Cl)cc5)n4)cc3C2)[C@@H]1OC]

Silica gel chromatography (CH$_2$Cl$_2$, then 30% EtOAc in CH$_2$Cl$_2$) provided the title compound (45 mg, 37%): $^1$H NMR (CDCl$_3$) δ 8.8 (d, 1H), 8.5 (d, 2H), 8.1 (d, 1H), 8.0 (m, 1H), 7.6 (d, 1H), 7.5 (d, 2H), 7.4 (d, 1H), 5.0 (s, 1H), 4.7 (m, 1H), 3.6-3.4 (m, 3H), 3.6 (s, 3H), 3.5 (s, 3H), 3.4 (s, 3H), 3.3-3.0 (m, 5H), 1.3 (d, 3H); ESIMS m/z 513 ([M+H+2]$^+$, 40), 511 ([M+H]$^+$, 100), 545 ([M+H]$^+$, 100).

2-(2,4-Dichlorophenyl)-4-[2-((2R,3R,4R,5S,6S)-3,4,5-trimethoxy-6-methyl-tetrahydropyran-2-yloxy)-indan-5-yl]-pyrimidine (Compound 2C)

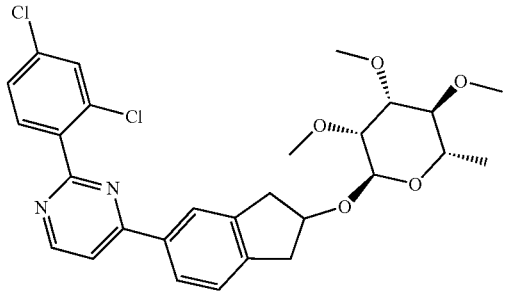 [SMILES: CO[C@@H]1[C@@H](OC)[C@H](C)O[C@@H](OC2Cc3ccc(-c4ccnc(-c5ccc(Cl)cc5Cl)n4)cc3C2)[C@@H]1OC]

Silica gel chromatography (3:2 CH$_2$Cl$_2$/EtOAc) afforded the title compound (55 mg, 27%): $^1$H NMR (CDCl$_3$) δ 8.86 (d, J=5.3 Hz, 1H), 8.06 (d, J=7.6 Hz, 1H,), 7.97 (m, 1H), 7.84 (dd, J=8.2, 1.3 Hz, 1H), 7.66 (d, J=5.3 Hz, 1H), 7.56 (d, J=2.0 Hz, 1H), 7.40-7.35 (m, 2H), 5.00 (s, 1H), 4.67 (m, 1H), 3.62-3.42 (m, 3H), 3.55 (s, 3H), 3.51 (s, 3H), 3.45 (s, 3H), 3.30-3.05 (m, 5H), 1.32 (d, J=6.3 Hz, 3H); ESIMS m/z 549 ([M+H+4]$^+$, 15), 547 ([M+H+2]$^+$, 71), 545 ([M+H]$^+$, 100);

Anal. Calcd for $C_{28}H_{30}Cl_2N_2O_5$: C, 61.65; H, 5.54; N, 5.14. Found: C, 61.37; H, 5.38; N, 5.12.

2-(3-Trifluoromethylphenyl)-4-[2-((2R,3R,4R,5S,6S)-3,4,5-trimethoxy-6-methyl-tetrahydropyran-2-yloxy)-indan-5-yl]-pyrimidine (Compound 3C)

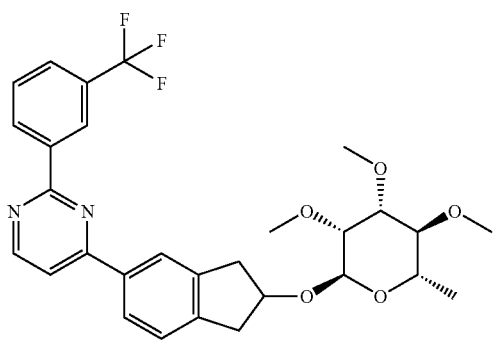 [SMILES: CO[C@@H]1[C@@H](OC)[C@H](C)O[C@@H](OC2Cc3ccc(-c4ccnc(-c5cccc(C(F)(F)F)c5)n4)cc3C2)[C@@H]1OC]

Reverse-phase liquid chromatography ($C_{18}$ amide linker-modified silica; gradient method proceeding from 3:2 $H_2O$/$CH_3CN$ to 95:5 $CH_3CN$/$H_2O$ containing 0.1% acetic acid) provided the title compound (20 mg, 15%): $^1$H NMR (CDCl$_3$) δ 8.85 (s, 1H), 8.84 (d, J=5.2 Hz, 1H), 8.78 (d, J=7.3 Hz, 1H), 8.06 (d, J=10.9 Hz, 1H), 8.02 (m, 1H), 7.76 (d, J=8.6 Hz, 1H), 7.64 (m, 1H), 7.63 (d, J=5.3 Hz, 1H), 7.39 (d, J=7.6 Hz, 1H), 5.01 (m, 1H), 4.70 (m, 1H), 3.63-3.43 (m, 3H), 3.56 (s, 3H), 3.52 (s, 3H), 3.46 (s, 3H), 3.32-3.07 (m, 5H), 1.33 (d, J=6.3 Hz, 3H); ESIMS m/z 544 ([M+H]$^+$, 100).

2-(4-Trifluoromethylphenyl)-4-[2-((2R,3R,4R,5S,6S)-3,4,5-trimethoxy-6-methyl-tetrahydropyran-2-yloxy)-indan-5-yl]-pyrimidine (Compound 4C)

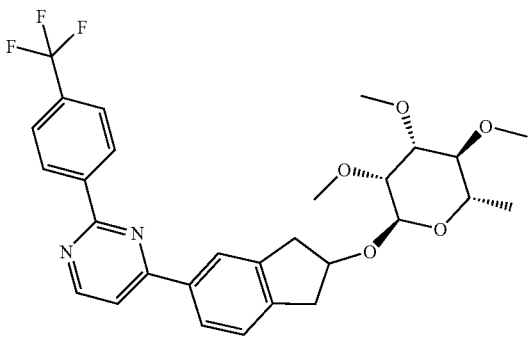 [SMILES: CO[C@@H]1[C@@H](OC)[C@H](C)O[C@@H](OC2Cc3ccc(-c4ccnc(-c5ccc(C(F)(F)F)cc5)n4)cc3C2)[C@@H]1OC]

Reverse-phase liquid chromatography ($C_{18}$ amide linker-modified silica; gradient method proceeding from 3:2 $H_2O$/$CH_3CN$ to 95:5 $CH_3CN$/$H_2O$ containing 0.1% acetic acid) provided the title compound (27 mg, 21%): $^1$H NMR (CDCl$_3$) δ 8.84 (d, J=5.3 Hz, 1H), 8.69 (d, J=8.3 Hz, 2H), 8.10 (d, J=9.2 Hz, 1H), 8.02 (m, 1H), 7.77 (d, J=8.6 Hz, 2H), 7.63 (d, J=5.3 Hz, 1H), 7.39 (d, J=7.9 Hz, 1H), 5.01 (m, 1H), 4.69 (m, 1H), 3.62-3.43 (m, 3H), 3.56 (s, 3H), 3.52 (s, 3H), 3.46 (s, 3H), 3.30-3.07 (m, 5H), 1.34 (d, J=6.3 Hz, 3H); ESIMS m/z 544 ([M+H]$^+$, 100).

Example 10

Preparation of 2-(4-methoxyphenyl)-4-[2-((2R,3R,4R,5S,6S)-3,4,5-trimethoxy-6-methyl-tetrahydropyran-2-yloxy)-indan-5-yl]-pyrimidine (Compound 5C)

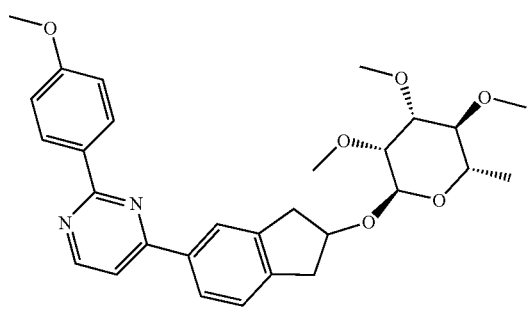

A solution of 3-dimethylamino-1-[2-(3,4,5-trimethoxy-6-methyl-tetrahydropyran-2-yloxy)-indan-5-yl]-propenone (Compound E-27; 100 mg, 0.238 mmol) and 4-methoxybenzamidine (107 mg, 0.715 mmol) in EtOH (3 mL) was heated at reflux overnight. The mixture was concentrated to a solid which was purified by silica gel chromatography (1:1 $CH_2Cl_2$/EtOAc) to afford the title compound (105 mg, 87%): $^1$H NMR (CDCl$_3$) δ 8.76 (d, J=5.2 Hz, 1H), 8.53 (d, J=9.0 Hz, 2H), 8.10 (d, J=8.7 Hz, 1H), 8.03-8.00 (m, 1H), 7.51 (d, J=5.4 Hz, 1H), 7.37 (d, J=8.0 Hz, 1H), 7.03 (d, J=9.0 Hz, 2H), 5.01 (m, 1H), 4.69 (m, 1H), 3.90 (s, 3H), 3.65-3.40 (m, 3H), 3.56 (s, 3H), 3.52 (s, 3H), 3.46 (s, 3H), 3.35-3.02 (m, 5H), 1.34 (d, J=6.2 Hz, 3H); ESIMS m/z 506 ([M+H]$^+$, 100).

The following compounds were prepared as in Example 10.

2-Pyridin-3-yl-4-[2-((2R,3R,4R,5S,6S)-3,4,5-trimethoxy-6-methyl-tetrahydropyran-2-yloxy)-indan-5-yl]-pyrimidine (Compound 6C)

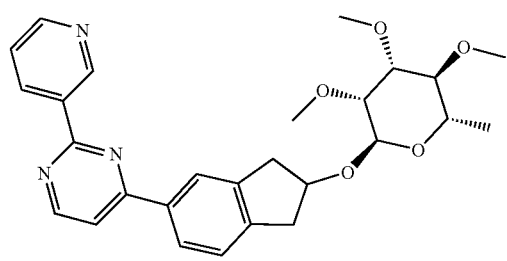 [SMILES: CO[C@@H]1[C@@H](OC)[C@H](C)O[C@@H](OC2Cc3ccc(-c4ccnc(-c5cccnc5)n4)cc3C2)[C@@H]1OC]

Silica gel chromatography (EtOAc) afforded the title compound (24 mg, 30%): $^1$H NMR (CDCl$_3$) δ 8.84 (d, J=5.4 Hz, 1H), 8.84-8.68 (m, 3H), 8.12 (d, J=11.0 Hz, 1H), 8.09 (m, 1H), 7.63 (d, J=5.4 Hz, 1H), 7.45 (m, 1H), 7.40 (d, J=7.8 Hz, 1H), 5.01 (m, 1H), 4.69 (m, 1H), 3.63-3.43 (m, 3H), 3.56 (s, 3H), 3.52 (s, 3H), 3.47 (s, 3H), 3.30-3.07 (m, 5H), 1.34 (d, J=6.2 Hz, 3H); ESIMS m/z 477 ([M+H]⁺, 100).

2-Phenyl-4-[2-((2R,3R,4R,5S,6S)-3,4,5-trimethoxy-6-methyl-tetrahydropyran-2-yloxy)-indan-5-yl]-pyrimidine (Compound 7C)

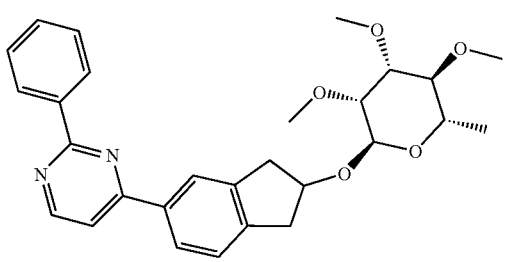 [SMILES: CO[C@@H]1[C@@H](OC)[C@H](C)O[C@@H](OC2Cc3ccc(-c4ccnc(-c5ccccc5)n4)cc3C2)[C@@H]1OC]

¹H NMR (CDCl₃) δ 8.82 (d, J=5.2 Hz, 1H), 8.59-8.56 (m, 2H), 8.12 (d, J=9.0 Hz, 1H), 8.02 (m, 1H), 7.58 (d, J=5.4 Hz, 1H), 7.53-7.51 (m, 3H), 7.38 (d, J=7.7 Hz, 1H), 5.01 (m, 1H), 4.69 (m, 1H), 3.65-3.44 (m, 3H), 3.56 (s, 3H), 3.52 (s, 3H), 3.47 (s, 3H), 3.30-3.07 (m, 5H), 1.33 (d, J=6.3 Hz, 3H); ESIMS m/z 477 ([M+H]⁺, 100).

Example 11

Preparation of 3-[2-((2R,3R,4R,5S,6S)-(3,4,5-trimethoxy-6-methyl-tetrahydropyran-2-yloxy)-indan-5-yl]-1H-pyrazole (Compound E-28)

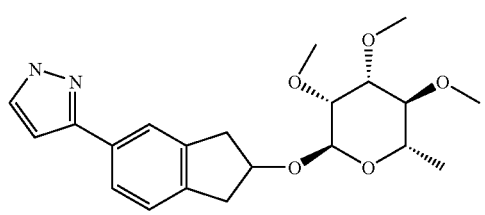 [SMILES: CO[C@@H]1[C@@H](OC)[C@H](C)O[C@@H](OC2Cc3ccc(-c4cc[nH]n4)cc3C2)[C@@H]1OC]

A solution of 3-dimethylamino-1-[2-(3,4,5-trimethoxy-6-methyl-tetrahydropyran-2-yloxy)-indan-5-yl]-propenone (Compound E-27; 98 mg, 0.234 mmol) and anhydrous hydrazine (50 pit) in MeOH (1 mL) was stirred at room temperature overnight. Concentration gave the title compound (68 mg, 75%): ¹H NMR (CDCl₃) δ 7.6 (m, 2H), 7.5 (m, 1H), 7.3 (m, 1H), 6.6 (s, 1H), 5.0 (s, 1H), 4.6 (m, 1H), 3.6-3.4 (m, 3H), 3.6 (s, 3H), 3.5 (s, 3H), 3.5 (s, 3H), 3.3-2.9 (m, 5H), 1.3 (d, J=6 Hz, 3H); ESIMS m/z 389 ([M+H]⁺).

Example 12

Preparation of 5-trifluoromethyl-2-{3-[2-((2R,3R,4R,5S,6S)-3,4,5-trimethoxy-6-methyl-tetrahydropyran-2-yloxy)-indan-5-yl]-pyrazol-1-yl}-pyridine (Compound 8C)

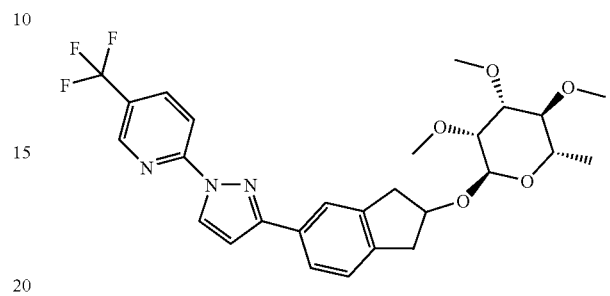

To a solution of Compound E-28 (97 mg, 0.25 mmol) in THF (1 mL) cooled in a dry ice/isopropyl alcohol bath was added dropwise via syringe a 1.0 M solution of lithium hexamethyldisilazide in THF (0.25 mL, 0.25 mmol). After 15 minutes (min), a solution of 2-fluoro-5-trifluoromethylpyridine (49 mg, 0.30 mmol) in THF (0.5 mL) was added dropwise via syringe. The contents were allowed to gradually warm to room temperature overnight with stirring. The solution was concentrated to a residue which was dissolved in Et₂O and was washed once with saturated NaHCO₃. The aqueous wash was extracted once with Et₂O and the combined extracts were dried (MgSO₄). Silica gel chromatography (CH₂Cl₂/EtOAc mixtures as eluent) afforded the title compound (73 mg, 55%): ¹H NMR (CDCl₃) δ 8.70 (m, 1H), 8.64 (d, J=2.7 Hz, 1H), 8.23 (m, 1H), 8.06 (m, 1H), 7.83 (s, 1H), 7.75 (d, J=7.7 Hz, 1H), 7.32 (d, J=8.0 Hz, 1H), 6.82 (d, J=2.8 Hz, 1H), 5.03 (s, 1H), 4.69 (m, 1H), 3.66-3.46 (m, 3H), 3.58 (s, 3H), 3.53 (s, 3H), 3.49 (s, 3H), 3.28-3.02 (m, 5H), 1.36 (2d, J=6.3 Hz, 3H); ESIMS m/z 534 ([M+H⁺]⁺, 40), 346 (100); Anal. Calcd for C₂₇H₃₀F₃N₃O₅: C, 60.78; H, 5.67; N, 7.88. Found: C, 60.69; H, 5.73; N, 7.78.

Example 13

Preparation of 2-trifluoromethyl-5-{3-[2-((2R,3R,4R,5S,6S)-3,4,5-trimethoxy-6-methyl-tetrahydropyran-2-yloxy)-indan-5-yl]-pyrazol-1-yl}-[1,3,4]thiadiazole (Compound 9C)

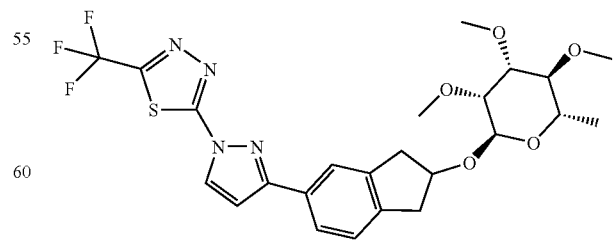

To a solution of 3-[2-(3,4,5-trimethoxy-6-methyl-tetrahydropyran-2-yloxy)-indan-5-yl]-1H-pyrazole (Compound E-28; 110 mg, 0.28 mmol) in THF (2 mL) cooled in a dry ice/isopropyl alcohol bath was added dropwise via syringe a 1.0 M solution of lithium hexamethyldisilazide in THF (0.28 mL, 0.28 mmol). After 15 min, a solution of 2-chloro-5-trifluoromethylthiadiazole (59 mg, 0.31 mmol) in THF (1.0 mL) was added dropwise via syringe. The contents were allowed to gradually warm to room temperature overnight with stirring. The solution was concentrated to a residue which was dissolved in $Et_2O$ and was washed once with saturated $NaHCO_3$. The aqueous wash was extracted once with $Et_2O$ and the combined extracts were dried ($MgSO_4$). Silica gel chromatography ($CH_2Cl_2$/EtOAc mixtures as eluent) afforded the title compound (104 mg, 68%): $^1$H NMR (CDCl$_3$) δ 8.49 (d, J=3.0 Hz, 1H), 7.77 (s, 1H), 7.70 (d, J=8.0 Hz, 1H), 7.33 (d, J=8.0 Hz, 1H), 6.89 (d, J=3.0 Hz, 1H), 5.02 (s, 1H), 4.68 (m, 1H), 3.66-3.45 (m, 3H), 3.58 (s, 3H), 3.53 (s, 3H), 3.49 (s, 3H), 3.30-2.99 (m, 5H), 1.35 (2d, J=6.3 Hz, 3H); ESIMS m/z 558 ([M+NH$_4$$^+$]$^+$, 100), 541 ([M+H]$^+$, 16); Anal. Calcd for $C_{24}H_{27}F_3N_4O_5S$: C, 53.32; H, 5.03; N, 10.36. Found: C, 53.30; H, 5.09; N, 10.24.

Example 14

Preparation of 4-[1-(4-Pentafluoroethyloxy-phenyl)-3-[2-((2R,3R,4R,5S,6S)-3,4,5-trimethoxy-6-methyl-tetrahydropyran-2-yloxy)-indan-5-yl]-1H-pyrazole (Compound 10C)

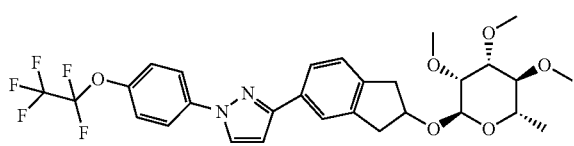 [SMILES: CO[C@@H]1[C@@H](OC)[C@H](C)O[C@@H](OC2Cc3ccc(-c4ccn(-c5ccc(OC(F)(F)C(F)(F)F)cc5)n4)cc3C2)[C@@H]1OC]

The pyrazole (Compound E-28; 38 mg, 0.099 mmol), 1-bromo-4-pentafluoroethyloxybenzene (35 mg, 0.119 mmol), $Cs_2CO_3$ (129 mg, 0.396 mmol), CuI (1 mg, 0.003 mmol), 8-hydroxyquinoline (1 mg, 0.003 mmol), and DMF/$H_2O$ (2 mL 10:1 solution) were combined in a 10 mL CEM Microwave reaction vessel fitted with magnetic stir bar and subjected to microwave irradiation at 150° C. for 30 min. The contents were then filtered and concentrated to dryness affording the title compound (14 mg, 0.023 mmol, 23%): $^1$H NMR (CDCl$_3$) δ 7.71 (d, J=3.36 Hz, 1H), 7.37 (d, J=8.29 Hz, 2H), 7.18 (d, J=8.29 Hz, 2H), 7.09 (d, J=8.38 Hz, 1H), 7.01 (s, 1H), 6.98 (d, J=8.38 Hz, 1H), 6.47 (d, J=3.36 Hz, 1H), 5.63 (d, J=1.85 Hz, 1H), 4.61 (m, 1H), 3.76 (dd, J=3.28, 1.99 Hz, 1H), 3.63 (m, 1H), 3.59 (s, 3H), 3.57 (s, 3H), 3.56 (s, 3H), 3.44 (dd, J=9.31, 3.36 Hz, 1H), 3.17 (t, J=9.48 Hz, 1H), 2.91 (m, 4H), 1.31 (d, J=6.26 Hz, 3H); EI/MS 598 m/e (M$^+$).

Testing of Compounds

Bioassays on beet armyworm (BAW; *Spodoptera exigua*: Lepidoptera) were conducted using either a 96-well microtiter plate-based high throughput (HTS) bioassay or a 128-well diet tray assay. The HTS assay is a based on a modification of Lewer et al. *J. Nat. Prod.* 2006, 69, 1506. BAW eggs were placed on top of artificial diet (100 microliters (μL)) in each well of 96-well microtiter plate. The diet was pretreated with test compounds (12 micrograms (μg) dissolved in 30 μL of DMSO-acetone-water mixture) layered on top of the diet using a liquid handling system and then allowed to dry for several hours. Infested plates were then covered with a layer of sterile cotton batting and the plate lid, and then held in the dark at 29° C. Mortality was recorded at 6 days (d) post-treatment. Each plate had six replicates. The percent mortality was calculated from the average of the six replicates. In the case of the 128-well diet assay, three to five second instar BAW larvae were placed in each well (3 mL) of the diet tray that had been previously filled with 1 mL of artificial diet to which 50 ug/cm$^2$ of the test compound (dissolved in 50 μL of 90:10 acetone/water mixture) had been applied (to each of eight wells) and then allowed to dry. Trays were covered with a clear self-adhesive cover, and held at 25° C., 14:10 light: dark for six days. Percent mortality was recorded for the larvae in each well; activity in the eight wells was then averaged. The results are indicated in Table 2. In Table 2 under both the BAW HTS and the BAW 50 headings, an "A" means that the compound was tested and at least 50 percent mortality was observed whereas, "B" means that either (1) the compound was tested and less than 50 percent mortality was observed or (2) the compound was not tested.

TABLE-I

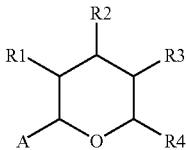

General Formula

| # | A | R1 | R2 | R3 | R4 | Sugar | M.S. | bp | $^1$H NMR (CDCl$_3$, δ) |
|---|---|----|----|----|----|-------|------|-----|------------------------|
| E-1 | OCH$_3$ | OCH$_3$ | OCH$_3$ | OCH$_3$ | CH$_3$ | L-rhamnose | | 150° C. (0.5 mm Hg) | 5.28 (m, 1H), 3.85 (m, 1H), 3.66 (m, 1H), 3.60-3.50 (m, 1H), 3.58 (s, 3H), 3.53 (s, 6H), 3.37 (s, 3H), 3.16 (t, 1H), 1.31 (d, J = 6.2 Hz, 3H) |
| E-2 | OH | OCH$_3$ | OCH$_3$ | OCH$_3$ | CH$_3$ | L-rhamnose | | 145-155° C. (1 mm Hg) | 5.28 (s, 1H), 3.83 (m, 1H), 3.7-3.45 (m, 11H), 3.16 (t, J = 9.2 Hz, 1H), 3.0 (s, 1H), 1.31 (d, J = 6 Hz, 3H) |
| E-3 | OCH$_3$ | OCH$_3$ | OC$_2$H$_5$ | OCH$_3$ | CH$_3$ | L-rhamnose | 202.9 (M − MeOH) | 165° C. (10 mTorr) | 4.71 (d, J = 1.8 Hz, 1H), 3.77-3.50 (m, 11H), 3.37 (s, 3H), 3.13 (t, J = 9.4 Hz, 1H), 1.32 (d, J = 6.3 Hz, 3H), 1.27 (t, J = 7.0 Hz, 3H) |

TABLE-I-continued

General Formula

| # | A | R1 | R2 | R3 | R4 | Sugar | M.S. | bp | ¹H NMR (CDCl₃, δ) |
|---|---|----|----|----|----|-------|------|----|-------------------|
| E-4 | OC₂H₅ | OC₂H₅ | OC₂H₅ | OC₂H₅ | CH₃ | L-rhamnose | 299.1 (M + Na) | 180° C. (10 mTorr) | 4.72 (d, J = 1.8 Hz) and 4.30 (s, total 1H), 4.0-3.35 (series of m, 10H), 3.2 (m, 2H), 1.3-1.1 (m, 15H) |
| E-5 | OCH₃ | OCH₃ | OC₃H₇ | OCH₃ | CH₃ | L-rhamnose |  | 175° C. (10 mTorr) | 4.70 (d, J = 1.8 Hz, 1H), 3.77-3.50 (m, 11H), 3.37 (s, 3H), 3.13 (t, J = 9.4 Hz, 1H), 1.62 (m, 2H), 1.32 (d, J = 6.3 Hz, 3H), 0.98 (t, J = 7.5 Hz, 3H) |
| E-6 | OCH₃ | OCH₃ | O-allyl | OCH₃ | CH₃ | L-rhamnose |  | 175° C. (10 mTorr) | 5.98 (m, 1H), 5.32 (d, 1H), 5.20 (d, 1H), 4.50 (s, 1H), 4.18 (d, 2H), 3.62-3.50 (m, 9H), 3.28 (s, 3H), 3.17 (t, J = 6.3 Hz, 1H), 1.33 (d, J = 6.3 Hz, 3H) |
| E-7 | OCH₃ | OCH₃ | OC₄H₉ | OCH₃ | CH₃ | L-rhamnose |  | 165° C. (5 mTorr) | 4.71 (s, 1H), 3.62-3.50 (m, 11H), 3.35 (s, 3H), 3.17 (t, 1H), 1.6 (m, 2H), 1.4 (m, 2H), 1.33 (d, J = 6.3 Hz, 3H), 0.98 (t, J = 7.5 Hz, 3H) |
| E-8 | OH | OCH₃ | OC₂H₅ | OCH₃ | CH₃ | L-rhamnose | 202.9 (M − H₂O) | 165° C. (9 mTorr) | 5.35 (m, J = 3.2, 2.0 Hz, 1H), 3.84-3.62 (m, 5H), 3.59 (s, 3H), 3.53 (s, 3H), 3.16 (t, J = 9.5 Hz, 1H), 2.73 (d, J = 3.4 Hz, 1H), 1.33-1.26 (m, 6H) |
| E-9 | OH | OC₂H₅ | OC₂H₅ | OC₂H₅ | CH₃ | L-rhamnose | 248.2 (M+) | 203° C. (5 mTorr) | 5.2 (s) and 4.65 (dd, J = 1.2, 9 Hz, anomeric proton signals, total 1H, ratio 64:36 α:β); 4.10-3.45 (m, 8H), 3.36-3.20 (m, 2H), 1.37-1.13 (m, 12H) |
| E-10 | OH | OCH₃ | OC₃H₇ | OCH₃ | CH₃ | L-rhamnose | 220.2 (M+) | 185° C. (5 mTorr) | 5.25 (dd, J = 3.2, 2.0 Hz) and 4.61 (m, total 1H), 3.80 (m, 1H), 3.70-3.50 (m, 9H), 3.36-3.05 (m, 1H), 1.60 (m, 2H), 1.30 (m, 5H), 0.95 (t, J = 7.5 Hz, 3H) |
| E-11 | OH | OCH₃ | O-allyl | OCH₃ | CH₃ | L-rhamnose | 254.9 (M + Na) | 175° C. (10 mTorr) | 5.95 (m, 1H), 5.3 (m, 1H), 5.19 (m, 1H), 5.21 and 4.61 (both m, α and β anomers, total 1H), 4.20 (m, 2H), 3.80 (m, 1H), 3.70-3.50 (m, 7H), 3.40-3.10 (m, 3H), 1.3 (m, 3H) |
| E-12 | OH | OCH₃ | OC₄H₉ | OCH₃ | CH₃ | L-rhamnose | 248.2 (M+) | 189° C. (5 mTorr) | 5.35 (dd, J = 3.2, 2.0 Hz) and 4.45 (m, total 1H), 3.80 (m, 1H), 3.70-3.50 (m, 10H), 3.36-3.05 (m, 1H), 2.73 (d, J = 3.4 Hz, 1H), 1.60 (m, 2H), 1.40 (m, 2H), 1.33 (d, J = 6 Hz, 3H), 0.95 (t, J = 7.5 Hz, 3H) |
| E-13 | —OH | —OCH₃ | —OCH₃ | —OCH₃ | CH₂O—CH₃ | L-mannose |  |  | 5.32 (s, 1H), 3.9 (m, 1H), 3.66-3.53 (series of m, 4H), 3.52 (s, 3H), 3.51 (s, 3H), 3.49 (s, 3H), 3.40 (s, 3H), 3.35 (m, 1H), 3.18 (d, J = 3 Hz, 1H) |
| E-14 | —OH | —OCH₃ | —OCH₃ | —OCH₃ | CH₂O—CH₃ | D-glucose |  |  | 5.33 (d, J = 3.6 Hz) and 4.60 (d, J = 4 Hz, α and β anomers, total 1H), 3.9 (m, 1H), 3.6-3.3 (series of s and m, 14H), 3.28 (m, 3H), 1.7 (s, 1H) |
| E-15 | —OCH₃ | —OCH₃ | —OCH₃ | —OCH₃ | —H₂ | L-xylose | 207 (M + H) |  | 4.77 (d, J = 3.5 Hz) and 4.15 (d, J = 7.4 Hz, total 1H in a 0.27:1 α:β ratio), 4.00 (dd, J = 11.6, 5.0 Hz, 1H), 4.03-2.93 (series of s and m, 16H) |
| E-16 | —OH | —OCH₃ | —OCH₃ | —OCH₃ | —H₂ | L-xylose | 175 (M − H₂O) |  | 5.23 (t, J = 3.4 Hz) and 4.60 (t, J = 6.3 Hz, total 1H in a 1.5:1 α:β ratio), 4.01-2.97 (series of s and m, 15H) |

TABLE-I-continued

General Formula

| # | A | R1 | R2 | R3 | R4 | Sugar | M.S. | bp | $^1$H NMR (CDCl$_3$, δ) |
|---|---|---|---|---|---|---|---|---|---|
| E-17 | —OCH$_3$ | —OCH$_3$ | —OCH$_3$ | —OCH$_3$ | —H$_2$ | L-lyxose | 207 (M + H) | | 4.69 (d, J = 3.0 Hz, 1H, β anomer), 3.77 (dd, J = 10.8, 4.7 Hz, 1H), 3.62-3.32 (series of s and m, 16H) |
| E-18 | —OH | —OCH$_3$ | —OCH$_3$ | —OCH$_3$ | —H$_2$ | L-lyxose | 175 (M − H$_2$O) | | 5.18-5.11 (m, 1H, mixture of α and β anomers), 4.84 (d, J = 10.1 Hz, 0.4H), 3.98-3.37 (series of s and m, 14H), 3.11 (d, J = 4.2 Hz, 0.6H) |
| E-19 | —OCH$_3$ | —OCH$_3$ | —OCH$_3$ | —OCH$_3$ | CH$_2$O—CH$_3$ | L-glucose | 205 (M − CH$_2$OCH$_3$) | | (600 MHz, CDCl$_3$) 4.83 (d, J = 4.1 Hz) and 4.14 (d, J = 7.8 Hz, total 1H in a 0.2:1 α:β ratio), 3.66-3.36 (series of s and m, 18H), 3.29-3.26 (m, 1H), 3.17-3.13 (m, 1H), 3.01-2.94 (m, 1H) |
| E-20 | —OH | —OCH$_3$ | —OCH$_3$ | —OCH$_3$ | CH$_2$O—CH$_3$ | L-glucose | 191 (M−CH$_2$OCH$_3$) | mp 63-67° C. | 5.33 (d, J = 3.7 Hz) and 4.58 (d, J = 7.9 Hz, total 1H in a 2.5:1 α:β ratio), 3.92-3.86 (m, 0.8H), 3.65-3.08 (series of s and m, 18H), 2.96 (dd, J = 8.8, 7.8 Hz, 0.2H) |
| E-21 | —OCH$_3$ | —H$_2$ | —OCH$_3$ | —OCH$_3$ | CH$_2$O—CH$_3$ | 2-deoxy-D-glucose | 220 (M$^+$) | | 4.81 (dd, J = 3.6, 1.1 Hz) and 4.34 (dd, J = 9.5, 1.9 Hz, total 1H in a 0.29:1 α:β ratio), 3.71-3.23 (m, 16H), 3.18-3.05 (m, 1H), 2.33-2.16 (m, 1H), 1.60-1.41 (m, 1H) |
| E-22 | —OCH$_3$ | —H$_2$ | —OCH$_3$ | OCH$_3$ | CH$_3$ | L-oleandrose | | | 4.78 (d, J = 3.3 Hz, 1H), 3.52 (m, 1H), 3.45 (s, 3H), 3.30 (s, 3H), 3.19 (m, 1H), 2.67 (br s, 1H), 2.29 (dd, J = 4.8, 12.9 Hz, 1H), 1.51 (m, 1H), 1.32 (d, J = 6.3 Hz, 3H) |

TABLE 2

| BAW 50 | BAW HTS | Compound | Ar | Het | R1 | R2 | R3 | R4 | anomer | sugar |
|---|---|---|---|---|---|---|---|---|---|---|
| A | B | 1C | 4-Cl-phenyl | pyrimidine (Ar–N=C(Ar$_2$)–N=CH–CH) | OCH$_3$ | OCH$_3$ | OCH$_3$ | CH$_3$ | α | L-rhamnose |
| B | A | 2C | 2,4-diCl-phenyl | pyrimidine (Ar–N=C(Ar$_2$)–N=CH–CH) | OCH$_3$ | OCH$_3$ | OCH$_3$ | CH$_3$ | α | L-rhamnose |

TABLE 2-continued

[Structure: Ar-Het-[indane]-O-[tetrahydropyran with R1, R2, R3, R4 substituents]]

| BAW 50 | BAW HTS | Compound | Ar | Het | R1 | R2 | R3 | R4 | anomer | sugar |
|---|---|---|---|---|---|---|---|---|---|---|
| A | B | 3C | 3-CF$_3$-phenyl | pyrimidine (Ar at 2, Ar$_2$ at 4) | OCH$_3$ | OCH$_3$ | OCH$_3$ | CH$_3$ | α | L-rhamnose |
| A | B | 4C | 4-CF$_3$-phenyl | pyrimidine (Ar at 2, Ar$_2$ at 4) | OCH$_3$ | OCH$_3$ | OCH$_3$ | CH$_3$ | α | L-rhamnose |
| A | A | 5C | 4-MeO-phenyl | pyrimidine (Ar at 2, Ar$_2$ at 4) | OCH$_3$ | OCH$_3$ | OCH$_3$ | CH$_3$ | α | L-rhamnose |
| B | B | 6C | 3-pyridyl | pyrimidine (Ar at 2, Ar$_2$ at 4) | OCH$_3$ | OCH$_3$ | OCH$_3$ | CH$_3$ | α | L-rhamnose |
| B | B | 7C | phenyl | pyrimidine (Ar at 2, Ar$_2$ at 4) | OCH$_3$ | OCH$_3$ | OCH$_3$ | CH$_3$ | α | L-rhamnose |
| A | A | 8C | 5-CF$_3$-pyridin-2-yl | pyrazole (N-Ar, Ar$_2$ at 3) | OCH$_3$ | OCH$_3$ | OCH$_3$ | CH$_3$ | α | L-rhamnose |
| A | A | 9C | 5-CF$_3$-1,3,4-thiadiazol-2-yl | pyrazole (N-Ar, Ar$_2$ at 3) | OCH$_3$ | OCH$_3$ | OCH$_3$ | CH$_3$ | α | L-rhamnose |
| A | A | 10C | 4-OC$_2$F$_5$-phenyl | pyrazole (N-Ar, Ar$_2$ at 3) | OCH$_3$ | OCH$_3$ | OCH$_3$ | CH$_3$ | α | L-rhamnose |

Acid & Salt Derivatives, and Solvates

The compounds disclosed in this invention can be in the form of pesticidally acceptable acid addition salts.

By way of non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic acids.

Additionally, by way of non-limiting example, an acid function can form salts including those derived from alkali or alkaline earth metals and those derived from ammonia and amines. Examples of preferred cations include sodium, potassium, magnesium, and aminium cations.

The salts are prepared by contacting the free base form with a sufficient amount of the desired acid to produce a salt. The free base forms may be regenerated by treating the salt with a suitable dilute aqueous base solution such as dilute aqueous sodium hydroxide (NaOH), potassium carbonate, ammonia, and sodium bicarbonate. As an example, in many cases, a pesticide is modified to a more water-soluble form e.g. (2,4-dichlorophenoxy)acetic acid dimethyl amine salt is a more water-soluble form of (2,4-dichlorophenoxy)acetic acid, a well known herbicide.

The compounds disclosed in this invention can also form stable complexes with solvent molecules that remain intact after the non-complexed solvent molecules are removed from the compounds. These complexes are often referred to as "solvates."

Stereoisomers

Certain compounds disclosed in this invention can exist as one or more stereoisomers. The various stereoisomers include geometric isomers, diastereomers, and enantiomers. Thus, the compounds disclosed in this invention include racemic mixtures, individual stereoisomers, and optically active mixtures. It will be appreciated by those skilled in the art that one stereoisomer may be more active than the others. Individual stereoisomers and optically active mixtures may be obtained by selective synthetic procedures, by conventional synthetic procedures using resolved starting materials, or by conventional resolution procedures.

Pests

In another embodiment, the invention disclosed in this document can be used to control pests.

In another embodiment, the invention disclosed in this document can be used to control pests of the Phylum Nematoda.

In another embodiment, the invention disclosed in this document can be used to control pests of the Phylum Arthropoda.

In another embodiment, the invention disclosed in this document can be used to control pests of the Subphylum Chelicerata.

In another embodiment, the invention disclosed in this document can be used to control pests of the Class Arachnida.

In another embodiment, the invention disclosed in this document can be used to control pests of the Subphylum Myriapoda.

In another embodiment, the invention disclosed in this document can be used to control pests of the Class Symphyla.

In another embodiment, the invention disclosed in this document can be used to control pests of the Subphylum Hexapoda.

In another embodiment, the invention disclosed in this document can be used to control pests of the Class Insecta.

In another embodiment, the invention disclosed in this document can be used to control Coleoptera (beetles). A non-exhaustive list of these pests includes, but is not limited to, *Acanthoscelides* spp. (weevils), *Acanthoscelides obtectus* (common bean weevil), *Agrilus planipennis* (emerald ash borer), *Agriotes* spp. (wireworms), *Anoplophora glabripennis* (Asian longhorned beetle), *Anthonomus* spp. (weevils), *Anthonomus grandis* (boll weevil), *Aphidius* spp., *Apion* spp. (weevils), *Apogonia* spp. (grubs), *Ataenius spretulus* (Black Turfgrass Ataenius), *Atomaria linearis* (pygmy mangold beetle), *Aulacophore* spp., *Bothynoderes punctiventris* (beet root weevil), *Bruchus* spp. (weevils), *Bruchus pisorum* (pea weevil), *Cacoesia* spp., *Callosobruchus maculatus* (southern cow pea weevil), *Carpophilus hemipteras* (dried fruit beetle), *Cassida vittata, Cerosterna* spp., *Cerotoma* spp. (chrysomelids), *Cerotoma trifurcata* (bean leaf beetle), *Ceutorhynchus* spp. (weevils), *Ceutorhynchus assimilis* (cabbage seedpod weevil), *Ceutorhynchus napi* (cabbage curculio), *Chaetocnema* spp. (chrysomelids), *Colaspis* spp. (soil beetles), *Conoderus scalaris, Conoderus stigmosus, Conotrachelus nenuphar* (plum curculio), *Cotinus nitidis* (Green June beetle), *Crioceris asparagi* (asparagus beetle), *Cryptolestes ferrugineus* (rusty grain beetle), *Cryptolestes pusillus* (flat grain beetle), *Cryptolestes turcicus* (Turkish grain beetle), *Ctenicera* spp. (wireworms), *Curculio* spp. (weevils), *Cyclocephala* spp. (grubs), *Cylindrocpturus adspersus* (sunflower stem weevil), *Deporaus marginatus* (mango leaf-cutting weevil), *Dermestes lardarius* (larder beetle), *Dermestes maculates* (hide beetle), *Diabrotica* spp. (chrysomelids), *Epilachna varivestis* (Mexican bean beetle), *Faustinus cubae, Hylobius pales* (pales weevil), *Hypera* spp. (weevils), *Hypera postica* (alfalfa weevil), *Hyperdoes* spp. (Hyperodes weevil), *Hypothenemus hampei* (coffee berry beetle), *Ips* spp. (engravers), *Lasioderma serricorne* (cigarette beetle), *Leptinotarsa decemlineata* (Colorado potato beetle), *Liogenys fuscus, Liogenys suturalis, Lissorhoptrus oryzophilus* (rice water weevil), *Lyctus* spp. (wood beetles/powder post beetles), *Maecolaspis joliveti, Megascelis* spp., *Melanotus communis, Meligethes* spp., *Meligethes aeneus* (blossom beetle), *Melolontha melolontha* (common European cockchafer), *Oberea brevis, Oberea linearis, Oryctes rhinoceros* (date palm beetle), *Oryzaephilus mercator* (merchant grain beetle), *Oryzaephilus surinamensis* (sawtoothed grain beetle), *Otiorhynchus* spp. (weevils), *Oulema melanopus* (cereal leaf beetle), *Oulema oryzae, Pantomorus* spp. (weevils), *Phyllophaga* spp. (May/June beetle), *Phyllophaga cuyabana, Phyllotreta* spp. (chrysomelids), *Phynchites* spp., *Popillia japonica* (Japanese beetle), *Prostephanus truncates* (larger grain borer), *Rhizopertha dominica* (lesser grain borer), *Rhizotrogus* spp. (European chafer), *Rhynchophorus* spp. (weevils), *Scolytus* spp. (wood beetles), *Shenophorus* spp. (Billbug), *Sitona lineatus* (pea leaf weevil), *Sitophilus* spp. (grain weevils), *Sitophilus granaries* (granary weevil), *Sitophilus oryzae* (rice weevil), *Stegobium paniceum* (drugstore beetle), *Tribolium* spp. (flour beetles), *Tribolium castaneum* (red flour beetle), *Tribolium confusum* (confused flour beetle), *Trogoderma variabile* (warehouse beetle), and *Zabrus tenebioides*.

In another embodiment, the invention disclosed in this document can be used to control Dermaptera (earwigs).

In another embodiment, the invention disclosed in this document can be used to control Dictyoptera (cockroaches). A non-exhaustive list of these pests includes, but is not limited to, *Blattella germanica* (German cockroach), *Blatta orientalis* (oriental cockroach), *Parcoblatta pennsylvanica, Periplaneta americana* (American cockroach), *Periplaneta australoasiae* (Australian cockroach), *Periplaneta brunnea* (brown cockroach), *Periplaneta fuliginosa* (smokybrown cockroach), *Pycnoscelus surinamensis* (Surinam cockroach), and *Supella longipalpa* (brownbanded cockroach).

In another embodiment, the invention disclosed in this document can be used to control Diptera (true flies). A non-exhaustive list of these pests includes, but is not limited to, *Aedes* spp. (mosquitoes), *Agromyza frontella* (alfalfa blotch leafminer), *Agromyza* spp. (leaf miner flies), *Anastrepha* spp. (fruit flies), *Anastrepha suspensa* (Caribbean fruit fly), *Anopheles* spp. (mosquitoes), *Batrocera* spp. (fruit flies), *Bactrocera cucurbitae* (melon fly), *Bactrocera dorsalis* (oriental fruit fly), *Ceratitis* spp. (fruit flies), *Ceratitis capitata* (Mediterranean fruit fly), *Chrysops* spp. (deer flies), *Cochliomyia* spp. (screwworms), *Contarinia* spp. (Gall midges), *Culex* spp. (mosquitoes), *Dasineura* spp. (gall midges), *Dasineura brassicae* (cabbage gall midge), *Delia* spp., *Delia platura* (seedcorn maggot), *Drosophila* spp. (vinegar flies), *Fannia* spp. (filth flies), *Fannia canicularis* (little house fly), *Fannia scalaris* (latrine fly), *Gasterophilus intestinalis* (horse bot fly), *Gracillia perseae, Haematobia irritans* (horn fly), *Hylemyia* spp. (root maggots), *Hypoderma lineatum* (common cattle grub), *Liriomyza* spp. (leafminer flies), *Liriomyza brassica* (serpentine leafminer), *Melophagus ovinus* (sheep ked), *Musca* spp. (muscid flies), *Musca autumnalis* (face fly), *Musca domestica* (house fly), *Oestrus ovis* (sheep bot fly), *Oscinella frit* (frit fly), *Pegomyia betae* (beet leafminer), *Phorbia* spp., *Psila rosae* (carrot rust fly), *Rhagoletis cerasi* (cherry fruit fly), *Rhagoletis pomonella* (apple maggot), *Sitodiplosis mosellana* (orange wheat blossom midge), *Stomoxys calcitrans* (stable fly), *Tabanus* spp. (horse flies), and *Tipula* spp. (crane flies).

In another embodiment, the invention disclosed in this document can be used to control Hemiptera (true bugs). A non-exhaustive list of these pests includes, but is not limited to, *Acrosternum hilare* (green stink bug), *Blissus leucopterus* (chinch bug), *Calocoris norvegicus* (potato mirid), *Cimex hemipterus* (tropical bed bug), *Cimex lectularius* (bed bug), *Dagbertus fasciatus, Dichelops furcatus, Dysdercus suturellus* (cotton stainer), *Edessa meditabunda, Eurygaster maura* (cereal bug), *Euschistus heros, Euschistus servus* (brown stink bug), *Helopeltis antonii, Helopeltis theivora* (tea blight plantbug), *Lagynotomus* spp. (stink bugs), *Leptocorisa oratorius, Leptocorisa varicornis, Lygus* spp. (plant bugs), *Lygus hesperus* (western tarnished plant bug), *Maconellicoccus hirsutus, Neurocolpus longirostris, Nezara viridula* (southern green stink bug), *Phytocoris* spp. (plant bugs), *Phytocoris californicus, Phytocoris relativus, Piezodorus guildingi, Poecilocapsus lineatus* (fourlined plant bug), *Psallus vaccinicola, Pseudacysta perseae, Scaptocoris castanea*, and *Triatoma* spp. (bloodsucking conenose bugs/kissing bugs).

In another embodiment, the invention disclosed in this document can be used to control Homoptera (aphids, scales, whiteflies, leafhoppers). A non-exhaustive list of these pests includes, but is not limited to, *Acrythosiphon pisum* (pea aphid), *Adelges* spp. (adelgids), *Aleurodes proletella* (cabbage whitefly), *Aleurodicus disperses, Aleurothrixus floccosus* (woolly whitefly), *Aluacaspis* spp., *Amrasca bigutella bigutella, Aphrophora* spp. (leafhoppers), *Aonidiella aurantii* (California red scale), *Aphis* spp. (aphids), *Aphis gossypii* (cotton aphid), *Aphis pomi* (apple aphid), *Aulacorthum solani* (foxglove aphid), *Bemisia* spp. (whiteflies), *Bemisia argentifolii, Bemisia tabaci* (sweetpotato whitefly), *Brachycolus noxius* (Russian aphid), *Brachycorynella asparagi* (asparagus aphid), *Brevennia rehi, Brevicoryne brassicae* (cabbage aphid), *Ceroplastes* spp. (scales), *Ceroplastes rubens* (red wax scale), *Chionaspis* spp. (scales), *Chrysomphalus* spp. (scales), *Coccus* spp. (scales), *Dysaphis plantaginea* (rosy apple aphid), *Empoasca* spp. (leafhoppers), *Eriosoma lanigerum* (woolly apple aphid), *Icerya purchasi* (cottony cushion scale), *Idioscopus nitidulus* (mango leafhopper), *Laodelphax striatellus* (smaller brown planthopper), *Lepidosaphes* spp., *Macrosiphum* spp., *Macrosiphum euphorbiae* (potato aphid), *Macrosiphum granarium* (English grain aphid), *Macrosiphum rosae* (rose aphid), *Macrosteles quadrilineatus* (aster leafhopper), *Mahanarva frimbiolata, Metopolophium dirhodum* (rose grain aphid), *Mictis longicornis, Myzus persicae* (green peach aphid), *Nephotettix* spp. (leafhoppers), *Nephotettix cinctipes* (green leafhopper), *Nilaparvata lugens* (brown planthopper), *Parlatoria pergandii* (chaff scale), *Parlatoria ziziphi* (ebony scale), *Peregrinus maidis* (corn delphacid), *Philaenus* spp. (spittlebugs), *Phylloxera vitifoliae* (grape phylloxera), *Physokermes piceae* (spruce bud scale), *Planococcus* spp. (mealybugs), *Pseudococcus* spp. (mealybugs), *Pseudococcus brevipes* (pine apple mealybug), *Quadraspidiotus perniciosus* (San Jose scale), *Rhapalosiphum* spp. (aphids), *Rhapalosiphum maida* (corn leaf aphid), *Rhapalosiphum padi* (oat bird-cherry aphid), *Saissetia* spp. (scales), *Saissetia oleae* (black scale), *Schizaphis graminum* (greenbug), *Sitobion avenae* (English grain aphid), *Sogatella furcifera* (white-backed planthopper), *Therioaphis* spp. (aphids), *Toumeyella* spp. (scales), *Toxoptera* spp. (aphids), *Trialeurodes* spp. (whiteflies), *Trialeurodes vaporariorum* (greenhouse whitefly), *Trialeurodes abutiloneus* (bandedwing whitefly), *Unaspis* spp. (scales), *Unaspis yanonensis* (arrowhead scale), and *Zulia entreriana*.

In another embodiment, the invention disclosed in this document can be used to control Hymenoptera (ants, wasps, and bees). A non-exhaustive list of these pests includes, but is not limited to, *Acromyrrmex* spp., *Athalia rosae, Atta* spp. (leafcutting ants), *Camponotus* spp. (carpenter ants), *Diprion* spp. (sawflies), *Formica* spp. (ants), *Iridomyrmex humilis* (Argentine ant), *Monomorium* spp., *Monomorium minumum* (little black ant), *Monomorium pharaonis* (Pharaoh ant), *Neodiprion* spp. (sawflies), *Pogonomyrmex* spp. (harvester ants), *Polistes* spp. (paper wasps), *Solenopsis* spp. (fire ants), *Tapoinoma sessile* (odorous house ant), *Tetranomorium* spp. (pavement ants), *Vespula* spp. (yellow jackets), and *Xylocopa* spp. (carpenter bees).

In another embodiment, the invention disclosed in this document can be used to control Isoptera (termites). A non-exhaustive list of these pests includes, but is not limited to, *Coptotermes* spp., *Coptotermes curvignathus, Coptotermes frenchii, Coptotermes formosanus* (Formosan subterranean termite), *Cornitermes* spp. (nasute termites), *Cryptotermes* spp. (drywood termites), *Heterotermes* spp. (desert subterranean termites), *Heterotermes aureus, Kalotermes* spp. (drywood termites), *Incistitermes* spp. (drywood termites), *Macrotermes* spp. (fungus growing termites), *Marginitermes* spp. (drywood termites), *Microcerotermes* spp. (harvester termites), *Microtermes obesi, Procornitermes* spp., *Reticulitermes* spp. (subterranean termites), *Reticulitermes banyulensis, Reticulitermes grassei, Reticulitermes flavipes* (eastern subterranean termite), *Reticulitermes hageni, Reticulitermes hesperus* (western subterranean termite), *Reticulitermes santonensis, Reticulitermes speratus, Reticulitermes tibialis, Reticulitermes virginicus, Schedorhinotermes* spp., and *Zootermopsis* spp. (rotten-wood termites).

In another embodiment, the invention disclosed in this document can be used to control Lepidoptera (moths and butterflies). A non-exhaustive list of these pests includes, but is not limited to, *Achoea janata, Adoxophyes* spp., *Adoxophyes orana, Agrotis* spp. (cutworms), *Agrotis ipsilon* (black cutworm), *Alabama argillacea* (cotton leafworm), *Amorbia cuneana, Amyelosis transitella* (navel orangeworm), *Anacamptodes defectaria, Anarsia lineatella* (peach twig borer), *Anomis sabulifera* (jute looper), *Anticarsia gemmatalis* (velvetbean caterpillar), *Archips argyrospila* (fruittree leafroller), *Archips rosana* (rose leaf roller), *Argyrotaenia* spp. (tortricid moths), *Argyrotaenia citrana* (orange tortrix), *Autographa gamma, Bonagota cranaodes, Borbo cinnara* (rice leaf folder), *Bucculatrix thurberiella* (cotton leafperforator), *Caloptilia* spp. (leaf miners), *Capua reticulana, Carposina niponensis* (peach fruit moth), *Chilo* spp., *Chlumetia transversa* (mango shoot borer), *Choristoneura rosaceana* (obliquebanded leafroller), *Chrysodeixis* spp., *Cnaphalocerus medinalis* (grass leafroller), *Colias* spp., *Conpomorpha cramerella, Cossus cossus* (carpenter moth), *Crambus* spp. (Sod webworms), *Cydia funebrana* (plum fruit moth), *Cydia molesta* (oriental fruit moth), *Cydia nignicana* (pea moth), *Cydia pomonella* (codling moth), *Darna diducta, Diaphania* spp. (stem borers), *Diatraea* spp. (stalk borers), *Diatraea saccharalis* (sugarcane borer), *Diatraea grandiosella* (southwestern corn borer), *Earias* spp. (bollworms), *Earias insulata* (Egyptian bollworm), *Earias vitella* (rough northern bollworm), *Ecdytopopha aurantianum, Elasmopalpus lignosellus* (lesser cornstalk borer), *Epiphysias postruttana* (light brown apple moth), *Ephestia* spp. (flour moths), *Ephestia cautella* (almond moth), *Ephestia elutella* (tobacco moth), *Ephestia kuehniella* (Mediterranean flour moth), *Epimeces* spp., *Epinotia aporema, Erionota thrax* (banana skipper), *Eupoecilia ambiguella* (grape berry moth), *Euxoa auxiliaris* (army cutworm), *Feltia* spp. (cutworms), *Gortyna* spp. (stemborers), *Grapholita molesta* (oriental fruit moth), *Hedylepta indicata* (bean leaf webber), *Helicoverpa* spp. (noctuid moths), *Helicoverpa armigera* (cotton bollworm), *Helicoverpa zea* (bollworm/corn earworm), *Heliothis* spp. (noctuid moths), *Heliothis virescens* (tobacco budworm), *Hellula undalis* (cabbage webworm), *Indarbela* spp. (root borers),

*Keiferia lycopersicella* (tomato pinworm), *Leucinodes orbonalis* (eggplant fruit borer), *Leucoptera malifoliella*, *Lithocollectis* spp., *Lobesia botrana* (grape fruit moth), *Loxagrotis* spp. (noctuid moths), *Loxagrotis albicosta* (western bean cutworm), *Lymantria dispar* (gypsy moth), *Lyonetia clerkella* (apple leaf miner), *Mahasena corbetti* (oil palm bagworm), *Malacosoma* spp. (tent caterpillars), *Mamestra brassicae* (cabbage armyworm), *Maruca testulalis* (bean pod borer), *Metisa plana* (bagworm), *Mythimna unipuncta* (true armyworm), *Neoleucinodes elegantalis* (small tomato borer), *Nymphula depunctalis* (rice caseworm), *Operophthera brumata* (winter moth), *Ostrinia nubilalis* (European corn borer), *Oxydia vesulia, Pandemis cerasana* (common currant tortrix), *Pandemis heparana* (brown apple tortrix), *Papilio demodocus, Pectinophora gossypiella* (pink bollworm), *Peridroma* spp. (cutworms), *Peridroma saucia* (variegated cutworm), *Perileucoptera coffeella* (white coffee leafminer), *Phthorimaea operculella* (potato tuber moth), *Phyllocnisitis citrella, Phyllonorycter* spp. (leafminers), *Pieris rapae* (imported cabbageworm), *Plathypena scabra, Plodia interpunctella* (Indian meal moth), *Plutella xylostella* (diamondback moth), *Polychrosis viteana* (grape berry moth), *Prays endocarpa, Prays oleae* (olive moth), *Pseudaletia* spp. (noctuid moths), *Pseudaletia unipunctata* (armyworm), *Pseudoplusia includens* (soybean looper), *Rachiplusia nu, Scirpophaga incertulas, Sesamia* spp. (stemborers), *Sesamia inferens* (pink rice stem borer), *Sesamia nonagrioides, Setora nitens, Sitotroga cerealella* (Angoumois grain moth), *Sparganothis pilleriana, Spodoptera* spp. (armyworms), *Spodoptera exigua* (beet armyworm), *Spodoptera frugiperda* (fall armyworm), *Spodoptera oridania* (southern armyworm), *Synanthedon* spp. (root borers), *Thecla basilides, Thermisia gemmatalis, Tineola bisselliella* (webbing clothes moth), *Trichoplusia ni* (cabbage looper), *Tuta absoluta, Yponomeuta* spp., *Zeuzera coffeae* (red branch borer), and *Zeuzera pyrina* (leopard moth).

In another embodiment, the invention disclosed in this document can be used to control *Mallophaga* (chewing lice). A non-exhaustive list of these pests includes, but is not limited to, *Bovicola ovis* (sheep biting louse), *Menacanthus stramineus* (chicken body louse), and *Menopon gallinae* (common hen louse).

In another embodiment, the invention disclosed in this document can be used to control Orthoptera (grasshoppers, locusts, and crickets). A non-exhaustive list of these pests includes, but is not limited to, *Anabrus simplex* (Mormon cricket), *Gryllotalpidae* (mole crickets), *Locusta migratoria, Melanoplus* spp. (grasshoppers), *Microcentrum retinerve* (angularwinged katydid), *Pterophylla* spp. (katydids), *Schistocerca gregaria, Scudderia furcata* (forktailed bush katydid), and *Valanga nigricornis*.

In another embodiment, the invention disclosed in this document can be used to control Phthiraptera (sucking lice). A non-exhaustive list of these pests includes, but is not limited to, *Haematopinus* spp. (cattle and hog lice), *Linognathus ovillus* (sheep louse), *Pediculus humanus capitis* (human body louse), *Pediculus humanus humanus* (human body lice), and *Pthirus pubis* (crab louse).

In another embodiment, the invention disclosed in this document can be used to control Siphonaptera (fleas). A non-exhaustive list of these pests includes, but is not limited to, *Ctenocephalides canis* (dog flea), *Ctenocephalides felis* (cat flea), and *Pulex irritans* (human flea).

In another embodiment, the invention disclosed in this document can be used to control Thysanoptera (thrips). A non-exhaustive list of these pests includes, but is not limited to, *Frankliniella fusca* (tobacco thrips), *Frankliniella occidentalis* (western flower thrips), *Frankliniella schultzei, Frankliniella williamsi* (corn thrips), *Heliothrips haemorrhaidalis* (greenhouse thrips), *Riphiphorothrips cruentatus, Scirtothrips* spp., *Scirtothrips citri* (citrus thrips), *Scirtothrips dorsalis* (yellow tea thrips), *Taeniothrips rhopalantennalis*, and *Thrips* spp.

In another embodiment, the invention disclosed in this document can be used to control Thysanura (bristletails). A non-exhaustive list of these pests includes, but is not limited to, *Lepisma* spp. (silverfish) and *Thermobia* spp. (firebrats).

In another embodiment, the invention disclosed in this document can be used to control Acarina (mites and ticks). A non-exhaustive list of these pests includes, but is not limited to, *Acarapsis woodi* (tracheal mite of honeybees), *Acarus* spp. (food mites), *Acarus siro* (grain mite), *Aceria mangiferae* (mango bud mite), *Aculops* spp., *Aculops lycopersici* (tomato russet mite), *Aculops pelekasi, Aculus pelekassi, Aculus schlechtendali* (apple rust mite), *Amblyomma americanum* (lone star tick), *Boophilus* spp. (ticks), *Brevipalpus obovatus* (privet mite), *Brevipalpus phoenicis* (red and black flat mite), *Demodex* spp. (mange mites), *Dermacentor* spp. (hard ticks), *Dermacentor variabilis* (american dog tick), *Dermatophagoides pteronyssinus* (house dust mite), *Eotetranycus* spp., *Eotetranychus carpini* (yellow spider mite), *Epitimerus* spp., *Eriophyes* spp., *Ixodes* spp. (ticks), *Metatetranycus* spp., *Notoedres cati, Oligonychus* spp., *Oligonychus coffee, Oligonychus ilicus* (southern red mite), *Panonychus* spp., *Panonychus citri* (citrus red mite), *Panonychus ulmi* (European red mite), *Phyllocoptruta oleivora* (citrus rust mite), *Polyphagotarsonemun latus* (broad mite), *Rhipicephalus sanguineus* (brown dog tick), *Rhizoglyphus* spp. (bulb mites), *Sarcoptes scabiei* (itch mite), *Tegolophus perseaflorae, Tetranychus* spp., *Tetranychus urticae* (twospotted spider mite), and *Varroa destructor* (honey bee mite).

In another embodiment, the invention disclosed in this document can be used to control Nematoda (nematodes). A non-exhaustive list of these pests includes, but is not limited to, *Aphelenchoides* spp. (bud and leaf & pine wood nematodes), *Belonolaimus* spp. (sting nematodes), *Criconemella* spp. (ring nematodes), *Dirofilaria immitis* (dog heartworm), *Ditylenchus* spp. (stem and bulb nematodes), *Heterodera* spp. (cyst nematodes), *Heterodera zeae* (corn cyst nematode), *Hirschmanniella* spp. (root nematodes), *Hoplolaimus* spp. (lance nematodes), *Meloidogyne* spp. (root knot nematodes), *Meloidogyne incognita* (root knot nematode), *Onchocerca volvulus* (hook-tail worm), *Pratylenchus* spp. (lesion nematodes), *Radopholus* spp. (burrowing nematodes), and *Rotylenchus reniformis* (kidney-shaped nematode).

In another embodiment, the invention disclosed in this document can be used to control Symphyla (symphylans). A non-exhaustive list of these pests includes, but is not limited to, *Scutigerella immaculata*.

For more detailed information consult "Handbook of Pest Control—The Behavior, Life History, and Control of Household Pests" by Arnold Mallis, 9th Edition, copyright 2004 by GIE Media Inc.

Mixtures

Some of the pesticides that can be employed beneficially in combination with the invention disclosed in this document include, but are not limited to the following:

1,2-dichloropropane, 1,3-dichloropropene, abamectin, acephate, acequinocyl, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan AKD-1022, amidithion, amidoflumet, aminocarb, amiton, amitraz, anabasine, arsenous oxide, athidathion, azadirachtin, azamethiphos, azinphos-ethyl, azinphos-methyl, azobenzene, azocyclotin, azothoate,

*Bacillus thuringiensis*, barium hexafluorosilicate, barthrin, benclothiaz, bendiocarb, benfuracarb, benomyl, benoxafos, bensultap, benzoximate, benzyl benzoate, beta-cyfluthrin, beta-cypermethrin, bifenazate, bifenthrin, binapacryl, bioallethrin, bioethanomethrin, biopermethrin, bistrifluron, borax, boric acid, bromfenvinfos, bromo DDT, bromocyclen, bromophos, bromophos-ethyl, bromopropylate, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, chinomethionat, chlorantraniliprole, chlorbenside, chlorbicyclen, chlordane, chlordecone, chlordimeform, chlorethoxyfos, chlorfenapyr, chlorfenethol, chlorfenson, chlorfensulphide, chlorfenvinphos, chlorfluazuron, chlormephos, chlorobenzilate, 3-(4-chloro-2,6-dimethylphenyl)-4-hydroxy-8-oxa-1-azaspiro[4,5]dec-3-en-2-one, 3-(4'-chloro-2,4-dimethyl[1,1'-biphenyl]-3-yl)-4-hydroxy-8-oxa-1-azaspiro[4,5]dec-3-en-2-one, 4-[[(6-chloro-3-pyridinyl)methyl]methylamino]-2(5H)-furanone, 4-[[(6-chloro-3-pyridinyl)methyl]cyclopropylamino]-2(5H)-furanone, 3-chloro-N2-[(1S)-1-methyl-2-(methylsulfonyl)ethyl]-N1-[2-methyl-4-[1,2,2,2-tetrafluoro-1-(trifluoromethyl)ethyl]phenyl]-1,2-benzenedicarboxamide, chloroform, chloromebuform, chloromethiuron, chloropicrin, chloropropylate, chlorphoxim, chlorprazophos, chlorpyrifos, chlorpyrifos-methyl, chlorthiophos, chromafenozide, cinerin I, cinerin II, cis-methrin, cloethocarb, clofentezine, closantel, clothianidin, copper acetoarsenite, copper arsenate, copper naphthenate, copper oleate, coumaphos, coumithoate, crotamiton, crotoxyphos, cruentaren A & B, crufomate, cryolite, cyanofenphos, cyanophos, cyanthoate, cyanthraniliprole, cyclethrin, cycloprothrin, cyenopyrafen, cyflumetofen, cyfluthrin, cyhalothrin, cyhexatin, cypermethrin, cyphenothrin, cyromazine, cythioate, 2-cyano-N-ethyl-4-fluoro-3-methoxy-benenesulfonamide, 2-cyano-N-ethyl-3-methoxy-benzenesulfonamide, 2-cyano-3-difluoromethoxy-N-ethyl-4-fluoro-benzenesulfonamide, 2-cyano-3-fluoromethoxy-N-ethyl-benzenesulfonamide, 2-cyano-6-fluoro-3-methoxy-N,N-dimethyl-benzenesulfonamide, 2-cyano-N-ethyl-6-fluoro-3-methoxy-N-methyl-benzenesulfonamide, 2-cyano-3-difluoromethoxy-N,N-dimethyl-benzenesulfonamide, d-limonene, dazomet, DBCP, DCIP, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diamidafos, diazinon, dicapthon, dichlofenthion, dichlofluanid, dichlorvos, dicofol, dicresyl, dicrotophos, dicyclanil, dieldrin, dienochlor, diflovidazin, diflubenzuron, 3-(difluoromethyl)-N-[2-(3,3-dimethylbutyl)phenyl]-1-methyl-1H-pyrazole-4-carboxamide dilor, dimefluthrin, dimefox, dimetan, dimethoate, dimethrin, dimethylvinphos, dimetilan, dinex, dinobuton, dinocap, dinocap-4, dinocap-6, dinocton, dinopenton, dinoprop, dinosam, dinosulfon, dinotefuran, dinoterbon, diofenolan, dioxabenzolos, dioxacarb, dioxathion, diphenyl sulfone, disulfuram, disulfoton, dithicrofos, DNOC, dofenapyn, doramectin, ecdysterone, emamectin, EMPC, empenthrin, endosulfan, endothion, endrin, EPN, epofenonane, eprinomectin, esfenvalerate, etaphos, ethiofencarb, ethion, ethiprole, ethoate methyl, ethoprophos, ethyl DDD, ethyl formate, ethylene dibromide, ethylene dichloride, ethylene oxide, etofenprox, etoxazole, etrimfos, EXD, F1050, famphur, fenamiphos, fenazaflor, fenazaquin, fenbutatin oxide, fenchlorphos, fenethacarb, fenfluthrin, fenitrothion, fenobucarb fenothiocarb, fenoxacrim, fenoxycarb, fenpirithrin, fenpropathrin, fenpyroximate, fenson, fensulfothion, fenthion, fenthion-ethyl, fentrifanil, fenvalerate, fipronil, FKI-1033, flonicamid, fluacrypyrim, fluazuron, flubendiamide, flubenzimine, flucofuron, flucycloxuron, flucythrinate, fluenetil, flufenerim, flufenoxuron, flufenprox, flumethrin, fluorbenside, fluvalinate, fonofos, formetanate, formothion, formparanate, fosmethilan, fospirate, fosthiazate, fosthietan, fosthietan, furathiocarb, furethrin, furfural, gamma-cyhalothrin, gamma-HCH, halfenprox, halofenozide, HCH, HEOD, heptachlor, heptenophos, heterophos, hexaflumuron, hexythiazox, HHDN, hydramethylnon, hydrogen cyanide, hydroprene, hyquincarb, imicyafos, imidacloprid, imiprothrin, indoxacarb, iodomethane, IPSP, isamidofos, isazofos, isobenzan, isocarbophos, isodrin, isofenphos, isoprocarb, isoprothiolane, isothioate, isoxathion, ivermectin jasmolin I, jasmolin II, jodfenphos, juvenile hormone I, juvenile hormone II, juvenile hormone III, JS118 kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfen, mesulfenfos, metaflumizone, metam, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, MNAF, monocrotophos, morphothion, moxidectin, naftalofos, naled, naphthalene, N-ethyl-2,2-dimethylpropionamide-2-(2,6-dichloro-α,α,α-trifluoro-p-tolyl) hydrazone, N-ethyl-2,2-dichloro-1-methylcyclopropane-carboxamide-2-(2,6-dichloro-α,α,α-trifluoro-p-tolyl) hydrazone, nicotine, nifluridide, nikkomycins, nitenpyram, nithiazine, nitrilacarb, novaluron, noviflumuron, omethoate, oxamyl, oxydemeton-methyl, oxydeprofos, oxydisulfoton, paradichlorobenzene, parathion, parathion-methyl, penfluoron, pentachlorophenol, permethrin, phenkapton, phenothrin, phenthoate, phorate, phosalone, phosfolan, phosmet, phosnichlor, phosphamidon, phosphine, phosphocarb, phoxim, phoxim methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, proclonol, profenofos, profluthrin, promacyl, promecarb, propaphos, propargite, propetamphos, propoxur, prothidathion, prothiofos, prothoate, protrifenbute, pyraclofos, pyrafluprole, pyrazophos, pyresmethrin, pyrethrin I, pyrethrin H, pyridaben, pyridalyl, pyridaphenthion, pyrifluquinazon, pyrimidifen, pyrimitate, pyriprole, pyriproxyfen, Qcide, quassia, quinalphos, quinalphos-methyl, quinothion, quantiofos, rafoxanide, resmethrin, rotenone, ryania, sabadilla, schradan, selamectin, silafluofen, sodium arsenite, sodium fluoride, sodium hexafluorosilicate, sodium thiocyanate, sophamide, spinetoram, spinosad, spirodiclofen, spiromesifen, spirotetramat, sulcofuron, sulfuram, sulfluramid, sulfotep, sulfoxaflor, sulfur, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetradifon, tetramethylfluthrin, tetramethrin, tetranactin, tetrasul, theta-cypermethrin, thiacloprid, thiamethoxam, thicrofos, thiocarboxime, thiocyclam, thiodicarb, thiofanox, thiometon, thionazin, thioquinox, thiosultap, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vamidothion, vaniliprole, vaniliprole, XMC, xylylcarb, zeta-cypermethrin and zolaprofos.

Additionally, any combination of the above pesticides can be used.

The invention disclosed in this document can also be used with herbicides and fungicides, both for reasons of economy and synergy.

The invention disclosed in this document can be used with antimicrobials, bactericides, defoliants, safeners, synergists, algaecides, attractants, desiccants, pheromones, repellants, animal dip, avicides, disinfectants, semiochemicals, and molluscicides (these categories not necessarily mutually exclusive) for reasons of economy, and synergy.

For more information consult "Compendium of Pesticide Common Names" located at http://www.alanwood.net/pesticides/index.html as of the filing date of this document. Also consult "The Pesticide Manual" 14$^{th}$ Edition, edited by C D S Tomlin, copyright 2006 by British Crop Production Council.

Synergistic Mixtures

The invention disclosed in this document can be used with other compounds such as the ones mentioned under the heading "Mixtures" to form synergistic mixtures where the mode of action of the compounds in the mixtures are the same, similar, or different.

Examples of modes of action include, but are not limited to: acetylcholinesterase inhibitor; sodium channel modulator; chitin biosynthesis inhibitor; GABA-gated chloride channel antagonist; GABA- and glutamate-gated chloride channel agonist; acetylcholine receptor agonist; MET I inhibitor; Mg-stimulated ATPase inhibitor; nicotinic acetylcholine receptor; Midgut membrane disrupter; and oxidative phosphorylation disrupter.

Additionally, the following compounds are known as synergists and can be used with the invention disclosed in this document: piperonyl butoxide, piprotal, propyl isome, sesamex, sesamolin, and sulfoxide.

Formulations

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra low volume solutions.

For further information on formulation types see "Catalogue of Pesticide Formulation Types and International Coding System" Technical Monograph no 2, 5$^{th}$ Edition by CropLife International (2002).

Pesticides are applied most often as aqueous suspensions or emulsions prepared from concentrated formulations of such pesticides. Such water-soluble, water-suspendable, or emulsifiable formulations, are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually chosen from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and nonionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional anionic and nonionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums, may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing, or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They are used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use this embodiment will be referred to as "OIWE."

For further information consult "Insect Pest Management" $2^{nd}$ Edition by D. Dent, copyright CAB International (2000). Additionally, for more detailed information consult "Handbook of Pest Control—The Behavior, Life History, and Control of Household Pests" by Arnold Mallis, $9^{th}$ Edition, copyright 2004 by GM Media Inc.

Other Formulation Components

Generally, the invention disclosed in this document when used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, antifoam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulphate; sodium dioctyl sulphosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulphonates. For suspension concentrates, very good adsorption and stabilization are obtained using polyelectrolytes, such as sodium naphthalene sulphonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulphonates; sodium naphthalene sulphonate formaldehyde condensates; tristyrylphenol ethoxylate phosphate esters; aliphatic alcohol ethoxylates; alky ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with 12 or more ethylene oxide units and the oil-soluble calcium salt of dodecylbenzene sulphonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The type of surfactants usually used for solubilization are non-ionics: sorbitan monooleates; sorbitan monooleate ethoxylates; and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alky ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, ULV formulations, and to a lesser extent granular formulations. Sometimes mixtures of solvents are used. The first main groups of solvents are aliphatic paraffinic oils such as kerosene or refined paraffins. The second main group and the most common comprises the aromatic solvents such as xylene and higher molecular weight fractions of $C_9$ and $C_{10}$ aromatic solvents. Chlorinated hydrocarbons are useful as cosolvents to prevent crystallization of pesticides when the formulation is emulsified into water. Alcohols are sometimes used as cosolvents to increase solvent power.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, e.g. bentonite; magnesium aluminum silicate; and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxy benzoic acid sodium salt; methyl p-hydroxy benzoate; and 1,2-benzisothiazolin-3-one (BIT).

The presence of surfactants, which lower interfacial tension, often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane while the non-silicone anti-foam agents are water-insoluble oils, such as octanol and nonanol, or silica. In both cases, the function of the anti-foam agent is to displace the surfactant from the air-water interface.

For further information see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

Applications

The actual amount of pesticide to be applied to loci of pests is not critical and can readily be determined by those skilled in the art. In general, concentrations from about 0.01 grams of pesticide per hectare to about 5000 grams of pesticide per hectare are expected to provide good control.

The locus to which a pesticide is applied can be any locus inhabited by a pest, for example, vegetable crops, fruit and nut trees, grape vines, ornamental plants, domesticated animals, the interior or exterior surfaces of buildings, and the soil around buildings.

Generally, with baits, the baits are placed in the ground where, for example, termites can come into contact with the bait. Baits can also be applied to a surface of a building, (horizontal, vertical, or slant surface) where, for example, ants, termites, cockroaches, and flies, can come into contact with the bait.

Because of the unique ability of the eggs of some pests to resist pesticides repeated applications may be desirable to control newly emerged larvae.

Systemic movement of pesticides in plants may be utilized to control pests on one portion of the plant by applying the pesticides to a different portion of the plant. For example, control of foliar-feeding insects can be controlled by drip irrigation or furrow application, or by treating the seed before planting. Seed treatment can be applied to all types of seeds, including those from which plants genetically transformed to express specialized traits will germinate. Representative examples include seeds or plants expressing proteins and/or double stranded RNA toxic to invertebrate pests, such as *Bacillus thuringiensis*, Bt Cry toxins, Bt Vip toxins, RNAi, or other insecticidal toxins, those expressing herbicide resistance, such as "Roundup Ready" seed, or those with "stacked" foreign genes expressing insecticidal toxins, herbicide resistance, nutrition-enhancement or any other beneficial traits. Furthermore, such seed treatments with the invention disclosed in this document can further enhance the ability of a plant to better withstand stressful growing conditions. This results in a healthier, more vigorous plant, which can lead to higher yields at harvest time.

It should be readily apparent that the invention can be used with plants genetically transformed to express specialized traits, such as *Bacillus thuringiensis*, RNAi, or other insecticidal toxins, or those expressing herbicide resistance, or those with "stacked" foreign genes expressing insecticidal toxins, herbicide resistance, nutrition-enhancement or any other beneficial traits.

The invention disclosed in this document is suitable for controlling endoparasites and ectoparasites in the veterinary medicine sector or in the field of animal keeping (which for the avoidance of doubt includes pets, for example, cats, dogs, and birds). Compounds according to the invention are applied here in a known manner, such as by oral administration in the form of, for example, tablets, capsules, drinks, granules, by dermal application in the form of, for example, dipping, spraying, pouring on, spotting on, and dusting, and by parenteral administration in the form of, for example, an injection.

The invention disclosed in this document can also be employed advantageously in livestock keeping, for example, cattle, sheep, pigs, chickens, and geese. Suitable formulations are administered orally to the animals with the drinking water or feed. The dosages and formulations that are suitable depend on the species.

Before a pesticide can be used or sold commercially, such pesticide undergoes lengthy evaluation processes by various governmental authorities (local, regional, state, national, international). Voluminous data requirements are specified by regulatory authorities and must be addressed through data generation and submission by the product registrant or by another on the product registrant's behalf. These governmental authorities then review such data and if a determination of safety is concluded, provide the potential user or seller with product registration approval. Thereafter, in that locality where the product registration is granted and supported, such user or seller may use or sell such pesticide.

The headings in this document are for convenience only and must not be used to interpret any portion thereof.

What is claimed is:

1. A compound having the following formula:

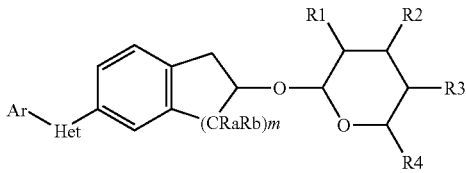

where

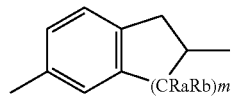

is referred to as Ar2
wherein:
(a) Ar is
(1) furanyl, phenyl, pyridazinyl, pyridyl, pyrimidinyl, thiadiazolyl, thienyl, or
(2) substituted furanyl, substituted phenyl, substituted pyridazinyl, substituted pyridyl, substituted pyrimidinyl, substituted thiadiazolyl, or substituted thienyl, wherein said substituted furanyl, substituted phenyl, substituted pyridazinyl, substituted pyridyl, substituted pyrimidinyl, substituted thiadiazolyl, and substituted thienyl, have one or more substituents independently selected from H, F, Cl, Br, I, CN, NO$_2$, C$_1$-C$_6$ alkyl, C$_1$-C$_6$ haloalkyl, C$_1$-C$_6$ hydroxyalkyl, C$_3$-C$_6$ cycloalkyl, C$_3$-C$_6$ halocycloalkyl, C$_3$-C$_6$ hydroxycycloalkyl, C$_3$-C$_6$ cycloalkoxy, C$_3$-C$_6$ halocycloalkoxy, C$_3$-C$_6$ hydroxycycloalkoxy, C$_1$-C$_6$ alkoxy, C$_1$-C$_6$ haloalkoxy, C$_2$-C$_6$ alkenyl, C$_2$-C$_6$ alkynyl, OSO$_2$(C$_1$-C$_6$ alkyl), OSO$_2$(C$_1$-C$_6$ haloalkyl), C(=O)H, C(=O)NR$_x$R$_y$, (C$_1$-C$_6$ alkyl)NR$_x$R$_y$, C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, phenoxy, substituted phenyl and substituted phenoxy, wherein such substituted phenyl and substituted phenoxy have one or more substituents independently selected from H, F, Cl, Br, I, CN, NO$_2$, C$_1$-C$_6$ alkyl, C$_1$-C$_6$ haloalkyl, C$_1$-C$_6$ hydroxyalkyl, C$_3$-C$_6$ cycloalkyl, C$_3$-C$_6$ halocycloalkyl, C$_3$-C$_6$ hydroxycycloalkyl, C$_3$-C$_6$ cycloalkoxy, C$_3$-C$_6$ halocycloalkoxy, C$_3$-C$_6$ hydroxycycloalkoxy, C$_1$-C$_6$ alkoxy, C$_1$-C$_6$ haloalkoxy, C$_2$-C$_6$ alkenyl, C$_2$-C$_6$ alkynyl, OSO$_2$(C$_1$-C$_6$ alkyl), OSO$_2$(C$_1$-C$_6$ haloalkyl), C(=O)H, C(=O)NR$_x$R$_y$, (C$_1$-C$_6$ alkyl)NR$_x$R$_y$, C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl)phenyl, and phenoxy;

(b) Het is a 5 or 6 membered, saturated or unsaturated, heterocyclic ring, containing one or more heteroatoms independently selected from nitrogen, sulfur, or oxygen, and where Ar and Ar$_2$ are not ortho to each other but may be meta or para, for a five membered ring they are 1,3 and for a 6 membered ring they are either 1, 3 or 1,4, and where said heterocyclic ring may also be substituted with one or more substituents independently selected from H, F, Cl, Br, I, CN, NO$_2$, oxo, C$_1$-C$_6$ alkyl, C$_1$-C$_6$ haloalkyl, C$_1$-C$_6$ hydroxyalkyl, C$_3$-C$_6$ cycloalkyl, C$_3$-C$_6$ halocycloalkyl, C$_3$-C$_6$ hydroxycycloalkyl, C$_3$-C$_6$ cycloalkoxy, C$_3$-C$_6$ halocycloalkoxy, C$_3$-C$_6$ hydroxycycloalkoxy, C$_1$-C$_6$ alkoxy, C$_1$-C$_6$ haloalkoxy, C$_2$-C$_6$ alkenyl, C$_2$-C$_6$ alkynyl, OSO$_2$(C$_1$-C$_6$ alkyl), OSO$_2$(C$_1$-C$_6$ haloalkyl), C(=O)H, C(=O)NR$_x$R$_y$, (C$_1$-C$_6$ alkyl)NR$_x$R$_y$, C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, phenoxy, substituted phenyl and substituted phenoxy wherein such substituted phenyl and substituted phenoxy have one or more substituents independently selected from H, F, Cl, Br, I, CN, NO$_2$, C$_1$-C$_6$ alkyl, C$_1$-C$_6$ haloalkyl, C$_1$-C$_6$ hydroxyalkyl, C$_3$-C$_6$ cycloalkyl, C$_3$-C$_6$ halocycloalkyl, C$_3$-C$_6$ hydroxycycloalkyl, C$_3$-C$_6$ cycloalkoxy, C$_3$-C$_6$ halocycloalkoxy, C$_3$-C$_6$ hydroxycycloalkoxy, C$_1$-C$_6$ alkoxy, C$_1$-C$_6$ haloalkoxy, C$_2$-C$_6$ alkenyl, C$_2$-C$_6$ alkynyl, OSO$_2$(C$_1$-C$_6$ alkyl), OSO$_2$(C$_1$-C$_6$ haloalkyl), C(=O)H, C(=O)NR$_x$R$_y$, (C$_1$-C$_6$ alkyl)NR$_x$R$_y$, C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, and phenoxy;

(c) R1 is H, OH, F, Cl, Br, I, oxo, C$_1$-C$_6$ alkyl, C$_1$-C$_6$ haloalkyl, C$_1$-C$_6$ alkoxy, C$_3$-C$_6$ cycloalkoxy, C$_1$-C$_6$ haloalkoxy, C$_2$-C$_6$ alkenyloxy, (C$_1$-C$_6$ alkyl)O(C$_1$-C$_6$ alkyl), (C$_1$-C$_6$ alkyl)O(C$_1$-C$_6$ alkoxy), OC(=O)(C$_1$-C$_6$ alkyl), OC(=O)(C$_3$-C$_6$ cycloalkyl), OC(=O)(C$_1$-C$_6$ haloalkyl), OC(=O)(C$_2$-C$_6$ alkenyl), or NR$_x$R$_y$;

(d) R2 is H, F, Cl, Br, I, oxo, C$_1$-C$_6$ alkyl, C$_1$-C$_6$ haloalkyl, C$_1$-C$_6$ alkoxy, C$_3$-C$_6$ cycloalkoxy, C$_1$-C$_6$ haloalkoxy, C$_2$-C$_6$ alkenyloxy, (C$_1$-C$_6$ alkyl)O(C$_1$-C$_6$ alkyl), (C$_1$-C$_6$ alkyl)O(C$_1$-C$_6$ alkoxy), OC(=O)(C$_1$-C$_6$ alkyl), OC(=O)(C$_3$-C$_6$ cycloalkyl), OC(=O)(C$_1$-C$_6$ haloalkyl), OC(=O)(C$_2$-C$_6$ alkenyl), or NR$_x$R$_y$;

(e) R3 is H, OH, F, Cl, Br, I, oxo, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_2$-$C_6$ alkenyloxy, ($C_1$-$C_6$ alkyl)O($C_1$-$C_6$ alkyl), ($C_1$-$C_6$ alkyl)O($C_1$-$C_6$ alkoxy), OC(=O)($C_1$-$C_6$ alkyl), OC(=O)($C_3$-$C_6$ cycloalkyl), OC(=O)($C_1$-$C_6$ haloalkyl), OC(=O)($C_2$-$C_6$ alkenyl), or $NR_xR_y$;

(f) R4 is H, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyloxy, ($C_1$-$C_6$ alkyl)O($C_1$-$C_6$ alkyl);

(g) m is 1 or 2;

(h) $R_x$ and $R_y$ are independently selected from H, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $OSO_2$($C_1$-$C_6$ alkyl), $OSO_2$($C_1$-$C_6$ haloalkyl), C(=O)H, C(=O)OH, C(=O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), phenyl, and phenoxy; and (i) $R_a$ and $R_b$ are independently selected from H, $C_1$-$C_6$ alkyl, $C_1$-$C_6$ haloalkyl, $C_1$-$C_6$ hydroxyalkyl, $C_1$-$C_6$ alkoxy, and $C_1$-$C_6$ haloalkoxy.

2. A compound according to claim 1 wherein said compound is selected from the group consisting of

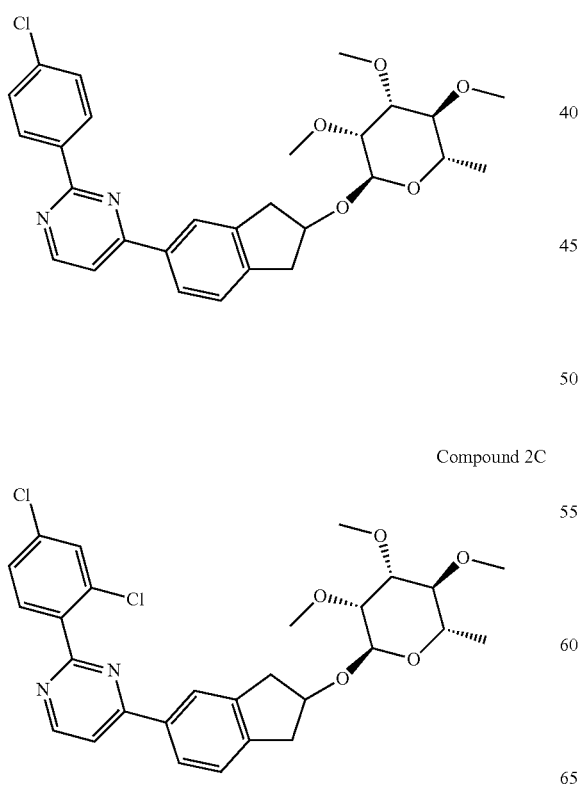

Compound 1C

Compound 2C

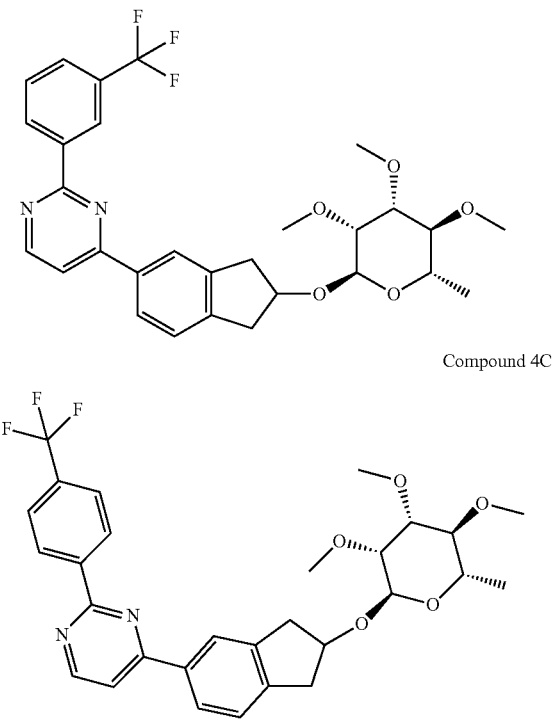

Compound 3C

Compound 4C

Compound 5C

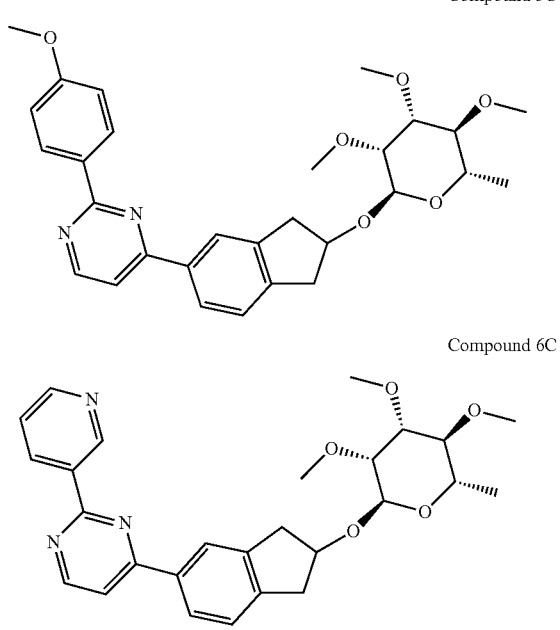

Compound 6C

Compound 7C

Compound 8C
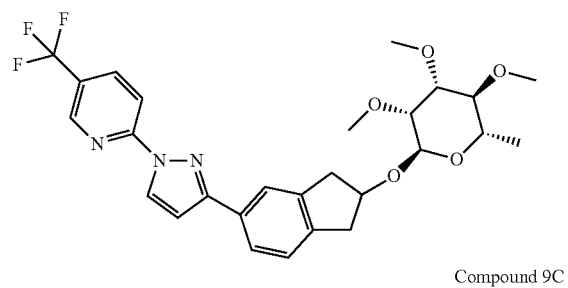
and
Compound 10C
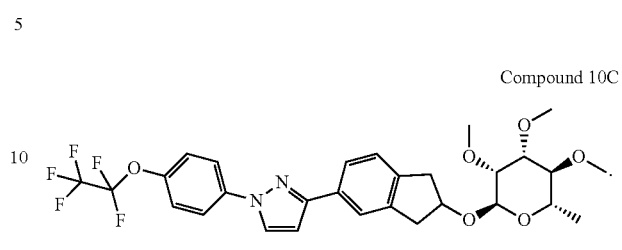
Compound 9C
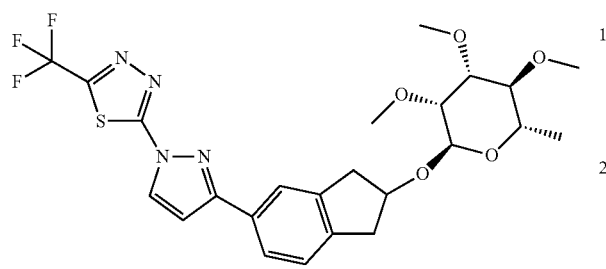
3. A compound that is a pesticidally acceptable acid addition salt of a compound according to claim 2.
4. A composition comprising a mixture of a compound according to claim 2 with at least one other pesticide.
\* \* \* \* \*